United States Patent [19]
Gozzini et al.

[11] Patent Number: 5,886,110
[45] Date of Patent: Mar. 23, 1999

[54] BINARY-BRANCHED POLYOXAALKYLENE MACROMOLECULES PROCESS FOR MAKING THEM AND THEIR USES

[75] Inventors: Luigia Gozzini; Monica Muttoni; Christoph De Haen, all of Milan, Italy

[73] Assignee: Dibra S.p.A., Italy

[21] Appl. No.: 69,958

[22] Filed: Apr. 30, 1998

Related U.S. Application Data

[62] Division of Ser. No. 404,259, Mar. 15, 1995, Pat. No. 5,780,644.

[30] Foreign Application Priority Data

Mar. 18, 1994 [IT] Italy ................................ MI94A0512

[51] Int. Cl.$^6$ ........................... C08F 283/00; C08G 4/00
[52] U.S. Cl. ......................... 525/472; 528/230; 528/248; 528/249; 528/265; 528/266; 528/310; 528/322; 528/373; 528/403; 525/509; 525/535; 525/540; 424/DIG. 16; 548/473; 548/478; 549/416
[58] Field of Search ..................... 528/230, 248, 528/249, 265, 266, 310, 322, 373, 403; 525/472, 509, 535, 540; 424/DIG. 16; 548/473, 478; 549/416

[56] References Cited

U.S. PATENT DOCUMENTS

| 4,289,872 | 9/1981 | Denkewalter et al. | 528/328 |
| 4,587,329 | 5/1986 | Tomalia et al. | 528/363 |
| 4,737,550 | 4/1988 | Tomalia | 525/418 |
| 5,041,516 | 8/1991 | Frechet et al. | 528/44 |
| 5,099,042 | 3/1992 | Wardle et al. | 552/11 |
| 5,294,365 | 3/1994 | Welch et al. | 252/174.21 |

*Primary Examiner*—Samuel A. Acquah
*Attorney, Agent, or Firm*—Nixon & Vanderhye

[57] ABSTRACT

Branched, dendrimeric macromolecules having a central nucleus and a series of polyoxaalkylene chains that radiate from the nucleus and spread into the surrounding space branching a cascade fashion until the desired size results. Molecules formed in this manner are free of excessive functional crowding on their outer surfaces. Synthetic methods of preparing these molecules and their uses are described.

4 Claims, No Drawings

BINARY-BRANCHED POLYOXAALKYLENE MACROMOLECULES PROCESS FOR MAKING THEM AND THEIR USES

This application is a continuation-in-part of application Ser. No. 08/404,259, filed 15 Mar. 1995, now U.S. Pat. No. 5,780,644.

The present invention concerns a new class of branched, dendrimeric macromolecules composed essentially of a central nucleus and of a series of polyoxaalkylene chains that depart from said nucleus and spread into the surrounding space branching in a cascade fashion until the desired size is obtained. The molecules formed in this way do not have excessive functional crowding on their outer surfaces. The invention also includes the synthetic method for obtaining these molecules as well as their uses.

Over the past decade dendrimeric macromolecules have stirred considerable interest because of their intrinsic features which are very different from those of highly polydispersed linear or branched polymers produced by polymerisation processes. In contrast, dendrimers are obtained through synthetic procedures involving a step-by-step growth, which allow for greater control over molecular mass, size and shape.

Dendrimeric molecules are characterized by having a central nucleus, termed "core", from which chains originate and branch off to the periphery to occupy all the available space. This leads to a multibranched ordered structure having many functional groups on the external surface. Such a molecule can have a highly congested surface capable of controlling the diffusion of small chemical entities into and out of the dendrimeric structure. Depending on the kind and dimension of their constituents, such macromolecules can assume different geometric shapes (spheroidal, cylindrical, mushroom-like, ellipsoidal etc.). Compared with other branched polymers, these macromolecules usually are endowed with a relatively low intrinsic viscosity (limiting viscosity number) even at high molecular masses.

Macromolecules with different denominations, synthetized and patented by different research groups can be included in this class of derivatives. The main classes are shown in Table I.

TABLE I

Main classes of dendrimeric macromolecules

| Denomination | Research group | References | Main patents | Chemical structures |
|---|---|---|---|---|
| Starburst | Tomalia | 1–5 | U.S. Pat. No. 4,587,329 | Starburst dendrimers include: polyamidoamines (PAMAM), polyethyleneimines (PEI), polyethers (PE) polythioethers. |
| Denkewalter dendrimers | Denkewalter | 6 | U.S. Pat. No. 4,289,872 | Lysine-based branched polymers. |
| Arborols | Newkome | 7–12, 29 | WO 9321144 | Arborols include molecules having either a benzene "core" or a "core" with four saturated hydrocarbon branches. |
| Dendrimeric polyethers | Fréchet | 13–19 | U.S. Pat. No. 5,041,516 WO 9208749 WO 9321259 | Functionalized benzenes synthetized through an original synthetic approach (convergent synthesis). |
| DSM dendrimers | De Brabander-van den Berg | 30 | WO 9314147 | Poly(propylene imine) dendrimers with branches prepared from vinyl cyanide units. |

Starburst dendrimers (Ref. 1–5)

Starburst dendrimers synthetized by Tomalia et al. include:

a) Starburst polyamidoamine (PAMAM) dendrimers (Ref. 1–3).

These are compounds with either a nucleophilic or an electrophilic "core". One of the most widely used nucleophilic "core" is ammonia. In this case, the synthesis involves a preliminary reaction with methyl acrylate (Michael's addition) to form a triester which is then amidated with ethylenediamine to form a first generation molecule containing 3 terminal amino groups (Scheme 1).

Scheme 1

$$NH_3 + CH_2=CH_2-COOMe \longrightarrow$$

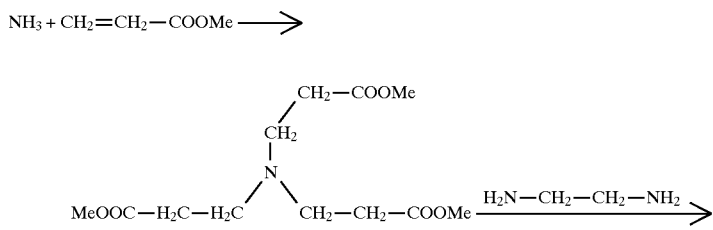

-continued
Scheme 1

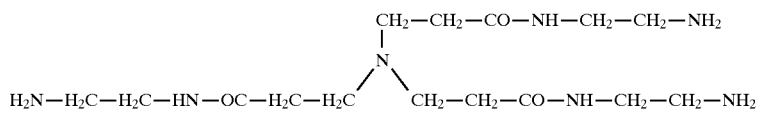

By repeating these synthetic steps the dendrimer grows in diameter by approximately 10 Å per generation evolving from an undefined shape for generations 0–2 to an oblate spheroid for generations 3–4 and finally to a nearly symmetrical spheroid for generations 5 and higher. Another example of "core" is ethylenediamine.

b) Starburst polyethyleneimine (PEI) dendrimers (Ref. 1).

These molecules derive from a symmetrical "core" comprising 3 amino functions, obtained through alkylation of diethylenetriamine with aziridine. The first generation is obtained by reacting this "core" with N-tosylaziridine or N-mesylaziridine and by subsequent deprotection (Scheme 2).

Scheme 2

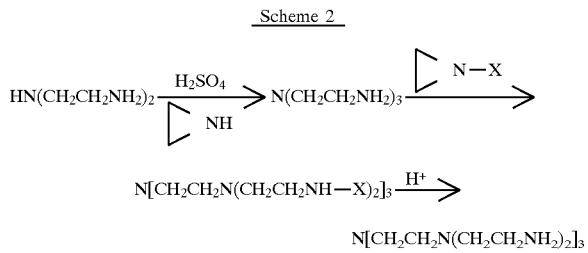

x = tosyl or mesyl

The higher generations are obtained by repeating these synthetic steps. PEIs differ from PAMAMs because of their short branch-segment lengths. For each generation, the diameter increases by only 5 Å compared with the 10 Å of PAMAMs. The CPK® (Corey Pauling Koltun) models indicate that these dendrimers are much more compact and congested than the starburst PAMAMs. These models show that the 5th generation results forbidden because of the so-called "dense-packing" phenomenon or excessive crowding of surface functional groups, phenomenon which makes impossible or only partially possible the further growth of the molecule (Ref. 1). Compared with PAMAMs, PEIs possess more stable chemical bonds.

c) Starburst polyether dendrimers (Ref. 1, 4, 5).

These dendrimers are examples of macromolecules endowed with the maximum packing effect due to the high multiplicity of the "core" (4 functional groups), and of the branching points (3 functional groups per unit). This gives rise to very compact molecules having highly congested microdomains which possess only very small internal voids. The starting molecule, pentaerythritol tetrabromide, is reacted with pentaerythritol molecules in which the 3 hydroxyl functions are protected as orthoesters. The resulting molecule assumes a spheroidal shape from the first generation. As a consequence by the fourth generation, which should possess 324 hydroxy groups on the external surface, a highly constrained and rigid system with no internal voids or channels should be formed. Indeed, the fourth generation cannot itself be obtained because of excessive steric hindrance on the external surface. Synthetic studies revealed that branching defects became progressively higher as one advanced from generation 2 to generation 3.

d) Starburst polythioether dendrimers (Ref. 1).

These are similar to the polyethers except that a mercaptobicyclic orthoester is used for the coupling step instead of the hydroxybicyclic orthoester. In this way, a dendrimer containing thioether bonds and hydroxyl groups on the external surface is obtained. In the case of polythioether dendrimers, the molecules are already hindered by the second generation and attempts to obtain the third generation have so far been unsuccessful. The main difference between PAMAMs and polyether and polythioether dendrimers is that the latter molecules assume a congested structure starting already from the first generation and have almost no internal voids. They are therefore much more compact molecules.

Denkewalter's dendrimers (Ref. 6).

Denkewalter et al. (Ref. 6) reported the synthesis of lysine-based dendrimers obtained by using the classic approach for solid-phase peptide synthesis. The lysine trees were constructed using a benzhydrylamine resin and N-protected tert-butyloxycarbonyl lysine. The branching points, i.e. the lysine amino groups, are located on segments of different length.

Polyamidoalcohol dendrimers (arborols) (Ref. 7–12, 29).

They have been synthetized by Newkome and co-workers. This class of dendrimers is an example of a heterogeneous series of highly branched compounds with a large number of functional groups on the external surface. In the literature, only low-generation molecules are described, usually of just first or second generation. The cascade polymers have been synthetized starting either from a benzene ring, to which three cascade spheres are attached, or from alkylhalides with a single cascade sphere. More recently, arborols with a skeleton consisting of saturated hydrocarbon chains with external hydrophilic groups, have been developed. These macromolecules can host non-polar molecules in their lipophilic cavities and may thus be regarded as unimolecular micelles.

Polyether dendrimers (Ref. 13–19).

These derivatives have been synthetized by Frechet and co-workers through an original synthetic approach involving two distinct steps:

a) preparing preformed dendrimeric fragments containing a reactive group, termed the "focal point";
b) assembling the dendrimeric molecule through reaction of the fragment focal points with the "core", which consists of a polyfunctional molecule.

However, by this approach the synthesis of dendrimers of fourth and higher generations is difficult because the reactivity of the focal point is reduced due to steric hindrance. The propagation monomers of these molecules are constituted by polyfunctional benzenes and thus these molecules are endowed with a certain degree of rigidity.

The first attempts at synthetizing branched molecules date back to 1978 when Buhleier, Wehner, and Vögtle, (Ref. 20)

proposed a synthetic scheme that involved the frequent repetition of similar steps which would add successive branches to a starting molecule. In this way, compounds with increasingly growing cavity size were obtained. This process, termed "cascade-like" synthesis, used linear or cyclic mono or diamines as starting molecules which, by reaction with acrylonitrile followed by reduction, give rise to new branching points. Recently, other types of dendrimers have been synthetized. Miller et al. (Ref. 21) prepared a series of dendrimers, containing 4, 10, 22 or 46 benzene rings which possess symmetrical and rigid molecular structures. Such dendrimers are thermally stable and, with the exception of the sparingly soluble first generation, are soluble in organic solvents such as THF, toluene and chloroform. The author suggested the use of these products as standards for size-exclusion chromatography. Uchida et al. (Ref. 22) and Mathias and Carothers (Ref. 23) synthetized silicone-based dendrimers up to the third generation. However, for the dendrimers of Mathias and Carothers, the absolute molecular weight, molecular weight distribution and uniformity of branching are still unknown.

Dendrimers having charges within the cascade structure have been described by Rengan and Engel (Ref 24, 25). These are phosphonium or ammonium sites and only the first three generations have been synthetized. Morikawa et al. (Ref. 26) synthetized starburst dendrimers containing polysiloxane units up to the third generation whose potential applications could be as drug carriers. Nagasaki et al. (Ref. 27) described the synthesis of arborols with encapsulated crown ethers in the hope of producing compounds with novel physical properties such as the selectivity towards alkali metal ions, the allosteric effect in the metal-binding process, the conformational change induced by the metal-binding and the polyelectrolyte-like behaviour of the resulting metal complexes. However, none of these characteristics have so far been demonstrated. These dendrimers were synthetized by the convergent synthetic approach. Because of the insolubility of the first generation and the steric hindrance of functional groups on the molecule, the divergent approach was also examined but failed to give the desired molecules. To date only the second generation has been obtained.

Polynuclear transition metal complexes of dendrimeric nature have been synthetized by Serroni et al. (Ref. 28). Building repetition blocks are linked not only through covalent bonds but also through metal chelate bonds.

Brabander-van den Berg et al. (Ref. 30) synthetized poly(propylene imine) dendrimers up to the fifth generation. These dendrimers are obtained through repetitive double Michael addition of acrylonitrile to primary amines, followed by a heterogeneously catalyzed hydrogenation of the nitrites. These kinds of dendrimers are not sensitive to hydrolytic degradation and are stable at high temperature. The process by which they are prepared is suitable for large scale productions.

As already mentioned, dendrimers reported in the literature have been obtained by two different synthetic approaches:

a) divergent synthesis;
b) convergent synthesis.

The syntheses of most dendrimers have been accomplished using the divergent process. This implies that a polyfunctional molecule is used as a "core" and that, in order to introduce multiplicity, each functional group is bonded to a molecule which also comprises more than one protected reactive site ("propagation monomer"). A first generation dendrimer is thus formed which, by exhaustive addition of polyfunctionalized monomers, gives rise to the next generation and so on. Monomer protection/deprotection systems need to be used in order to perform the selective modification of specific groups at each synthetic step.

Convergent synthesis, as first proposed by Frechet, differs from the divergent approach in that growth starts at what will become the periphery of the macromolecule. Such a method results in the formation of large dendrimeric fragments, which ultimately are attached through a reactive group ("focal point") to a polyfunctional "core". Convergent synthesis has certain advantages over divergent synthesis. With divergent synthesis, the molecule's growth occurs through the simultaneous addition of an increasing number of reactive sites. With the convergent approach, on the other hand, size increase involves a limited number of reactive sites. Convergent synthesis makes use of a smaller excess of reagents. Possible side reactions are therefore avoided and the final products more easily purified. However, one limitation of the convergent approach is that, as the size of the dendrimers increases, there is an increase in the steric hindrance near the functional group, or focal point, which prevents the group from reacting with the "core". This limitation is also common in divergent synthesis since the size of the molecule increases more slowly than the number of external functional groups. This leads to an increase in steric hindrance around the functional groups which are thus prevented from reacting to give the next generation.

There are notable differences among the different types of dendrimers. With regard to the starburst dendrimers, PAMAM and the polyethers possess different multiplicity of the "core" (3 for PAMAM; 4 for the polyethers); as a result PAMAM are much less sterically hindered than the polyethers and show internal cavities. These characteristics allow the synthesis of PAMAM products with higher generation numbers than is possible with polyethers for which the phenomenon of "dense-packing" is already apparent by the third generation. On the other hand, the early generations of PAMAM dendrimers, unlike the polyethers, do not have definite shapes; only the more advanced generations of PAMAM dendrimers have definite shapes. In addition, the large excess of reagents (typically ethylenediamine) that are required for the synthesis of PAMAM can cause problems. In the early generations these reagents are easily removed. However, as dendrimers grow, the removal of these excesses becomes more difficult. The same is true for certain by-products which may arise from incomplete Michael addition reactions, from intramolecular cyclizations, from fragmentation due to retro-Michael reactions or from intermolecular cyclizations that result in the formation of bridges between two dendrimers. These problems are not seen with starburst polyethers where an excess of reagents is not necessary and where the dendrimers are crystalline. This makes the purification of polyether dendrimers much easier.

As regards L-lysine-based Denkewalter dendrimers, they have asymmetric "branches" and their structures have not been rigorously established. The different lengths of the "branches" can cause steric hindrance because a few functional groups are buried in the internal part of the molecule and therefore sterically hindered and unreactive.

Newkome et al. (Ref. 8–12, 29) have synthetized less branched, less sterically hindered molecules which have large lipophilic internal cavities capable of accepting hydrophobic molecules and which in solution behave similarly to micelles. The synthesis of such molecules is rather complex, because of the unreactivity of the neopentylic centre ("core") to nucleophilic reactions (Ref. 11). To overcome this drawback, the introduction of a "spacer" of at least 3 atoms was necessary.

The dendrimeric macromolecules described above have been synthetized with specific uses in mind. They could, for example, be used as transporters of high quantities of substances and it is for this reason that dendrimers are extensively studied as possible "carriers" for the controlled and targeted release of drugs. It is possible to prepare dendrimers with a lipophilic interior and a hydrophilic surface thus obtaining molecules that can function as micelles. Compared to micelles, such molecules, as a result of their intrinsic characteristics, could show much greater stability. By utilizing suitable monomers in the latter generation, it is theoretically possible to control the porosity of the external sphere of the molecule. In this regard, dendrimers can perhaps be compared with cells. Furthermore, these polymers are characterized by possessing large surface areas which, in combination with high solubility in organic solvents, might facilitate their use as carriers of catalyzers that could be recovered at the end of the reaction by simple extraction or filtration.

Compounds that are suitable for association with dendrimers are, in general, molecules that can be used either for therapeutic treatment or for in vivo or in vitro diagnosis. Compounds of this type are for example pharmaceuticals (such as antibiotics, analgesics, antihypertensives, and cardiotonics) used in the treatment of various diseases; radionuclides; signal generators and absorbers; antibodies; metal chelates; opacifying diagnostics and hormones. The in vivo and in vitro diagnostic procedures which could benefit from the use of dendrimer derivatives are, for example: radioimmunologic assays, electron microscopy, ELISA, X-ray imaging, magnetic resonance imaging (MRI) and immunoscintigraphy. Dendrimers can also have other uses, for example as "carriers" of chemical substances for agriculture, as adhesives, as absorbents, as oil/water demulsifiers, as thickeners of plastic materials, as calibration standards for ultrafiltration membranes and electron microscopy, as standards for size-exclusion chromatography, and as agents to modify the rheological properties of solutions of dyes and paints. Despite all these possible applications, however, none as yet have been fully realised. This is in part due to the difficulties in synthetizing dendrimers with a large number of generations (because of the "dense-packing" problem), and in part because of the difficulties in the synthesis of three-dimensional structures with adequate internal cavities, in terms of number and dimension, for the intended use.

The objects of the present invention are new, dendrimeric macromolecules that comprise the following structural groups:

a) a central "core", derived from a polyvalent organic molecule from which at least two polyoxaalkylene chains originate, b) at least two polyoxaalkylene chains, preferably polyoxaethylene or polyoxapropylene, that are connected to the above-mentioned "core", c) at least two polyvalent branched organic residues attached to the ends of said chains which function as branching points for the successive growth of the molecule, because each of these points can be reacted with two other polyoxaalkylene chains, d) possibly further polyoxaalkylene chains and branching points added in succession until the molecule reaches the desired dimension.

One polyoxaalkylene chain, taken together with its branching point, constitutes a growth, or repetition unit. The total amount of growth units comprised in the same growth level represents a generation shell.

Preferred polyoxaalkylene chains are polyoxaethylene chains, while the preferred degree of branching at each branching point is equal to 2.

The "core" is characterized by a multiplicity number which refers to the number of functional groups on the "core", that enable growth of the molecule. Preferred multiplicity number ranges from 3 to 5.

The introduction of the first branching point in the molecule determines the first generation, the introduction of a successive branching point determines the second generation and so on. The length of the polyoxaalkylene chain between the "core" and the first branching point, or between one branching point and the next one, can vary.

Such chain lengths are chosen according to the structure and the characteristics required for the macromolecule. For example, the chain length influences the formation of the internal cavities within the structure and/or the compactness (density) of the molecule, and in the early generations particularly, its geometric form as well. The preferred polyoxaethylene chains are characterized by the $-[OCH_2CH_2]_n-$ unit where n is a number from 0 to 25 and preferably from 0 to 15, provided that in at least one generation shell n is different from 0. The distance between the "core" and the first branching point, or between one branching point and next one, is determined by the length of the polyoxaethylene chain, i.e. by the value of n. This value can be equal in each generations or can vary from generation to generation.

The central nucleus of the compounds of the present invention can derive from any polyvalent, aliphatic organic open chain residue, both branched and not, or from alicyclic residues, or from heterocyclic residues containing N, O and/or S, or from aromatic or heteroaromatic residues. All of them are substituted by from 3 to 5 reactive groups to which the polyoxaethylene chains of the first generation are covalently attached. The "core" can also possess one or more reactive groups that do not participate to the growth of the molecule but which are possibly available for the coupling to other structures or as dimerization points. Strongly preferred examples of "core" include, among others, molecules with neopentylic centres (pentaerythritol, hydroxymethylpropantriol). Preferred branching points can consist of polyvalent residues with reactive functions suitable for binary branching. The multiplicity of the "core", and the value of n can be chosen according to the characteristics/properties desired in the final macromolecule. In this way it is possible to obtain macromolecules with different distributions of functional groups on the external surface: for example, zonal distribution if the polyoxaethylene chains connected to the "core" are long and those of the branches short, or uniform distribution if the polyoxaethylene chains are of equal length. In both cases there will be a different density of terminal groups and/or chains between the peripheral and the central part of the molecule. With the degrees of freedom conferred by the length of the polyoxaethylene chains and by the multiplicity of the "core", one can obtain macromolecules with internal cavities of different dimensions, which are either all equal or which vary from generation to generation. A further advantage arising from the introduction of polyoxaethylene chains between the "core" and the first branching point, or between one branching point and the next one, is that in this way it is possible to construct molecules that are able to grow further giving structures with a large number of generations. This is the fundamental point of the present invention. Additionally, it is also possible to avoid the phenomenon of "dense-packing", a phenomenon that severely hampers the preparation of the dendrimers of the prior-art by restricting the number of successive generations obtainable. As a general rule, one of the main obstacles to the synthesis of dendrimeric structures is the excessive surface area crowding that inevitably arises with higher numbers of generations. For this reason the growth of the structure becomes progressively more difficult. For example, preparation of molecules of the third generation, in the case of polythioethers, or of the fourth in the case of polyethers, is effectively impossible as reported by Tomalia (Ref. 1).

In contrast the adoption of polyoxaethylene chains enables the preparation of molecules with less compact structures. Further, the preferred introduction of binary branching points renders more feasible and convenient the industrial production of the desired molecules For these macromolecules, problems due to the inclusion of reagents and solvents during the various synthetic steps, phenomenon which can cause significant difficulty during the purification process, are very much reduced.

The external surfaces of the macromolecules of the present invention are well provided with functional groups such as for example hydroxyl, tosyl, mesyl, tresyl, brosyl and similar groups, trifluoromethanesulfonyl, phthalimido, amino, thiol, aldehydo, nitrilo, acetyl, pyranyl, cyclic orthoester, carboxyl and amido groups.

As a consequence, the compounds of the present invention may be ideally suited to the transport of drugs and/or molecules for use in diagnostic imaging. Both these classes of compounds can be linked to such macromolecules, either directly or through suitable spacer chains, alternatively they can be included in the macromolecules themselves. Concerning diagnostic imaging, it is, for example, possible to obtain contrast agents for magnetic resonance (MRI) by linking paramagnetic metal chelates, such as chelates of polyaminopolycarboxylic acids, to these molecules. In this respect they could represent a good solution to the development of new effective blood-pool agents. Ferromagnetic or superparamagnetic (ferrite, magnetites or derivatives thereof) compounds can also be included in the internal cavities of the macromolecules for diagnostic use in MRI.

The macromolecules of the present invention can also be linked to chelates of radioactive metal ions for use in nuclear medicine, or conjugated to iodinated molecules for use in all roentgenographic diagnostic investigations.

The molecules may also be labelled with isotopes such as $^{13}C$, $^{14}C$, $^{2}H$, $^{3}H$ or 125I and used subsequently in biodistribution studies. Moreover, they may be used in the preparation of pharmaceutical products where controlled release of the active principle is required. Moreover, it is even possible to modify the external functional groups with suitable hydrophobic groups to create a molecular structure that behaves as an inverse micelle, i.e. with a hydrophilic internal part and a hydrophobic surface. Moreover such macromolecules are highly promising as carriers of catalyzers, allowing a complete recovery of the same after the reaction. Finally, since the macromolecules of the present invention can be prepared to precise and define dimensions, they are particularly useful as calibration standards for separation techniques based on molecular shape, such as for example size-exclusion chromatography.

Accordingly, the compounds of the present invention are represented by the following formula (I)

$$A[G_{(1 \to p)}]_r \qquad (I),$$

having r number of structures $G_{(1 \to p)}$ in the dendrimer structure, where:

A is a polyfunctional/polyvalent central nucleus, or core, which is an aliphatic open chain, branched or unbranched, or an alicyclic, or a heterocyclic group containing N, O and/or S, or an aromatic or a heteroaromatic group and which contains terminal groups to which polyoxaethylene chains of a first generation shell are attached, r is an integer from 3 to 5 representing the multiplicity of the core, $G_{(1 \to p)}$ is a single dendron linked to A, $[G_{(1 \to p)}]_r$ represents the branched structure of the macromolecule comprising p levels of generation shells, from the first one $g_{(1)}$ to the last one $g_{(p)}$, in which the total number p of said generation shells can range from 1 to 20 and in which the different generation shells may contain the same repetition units, and in which:

(a) each generation $g_{(i)}$, except for the last $g_{(p)}$, comprises repeating units, which are represented by functional groups of formula

—B—M— where:

B is a polyoxaethylene chain of formula:

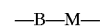

in which n can range from 0 to 25 and may differ from generation shell to generation shell and in which, in at least one generation shell of the macromolecule, n is other than 0, M represents a binary branching point, which is a polyvalent aliphatic group comprising 2 reactive functional groups for the linking of the polyoxaethylene chains of the next generation shell, (b) the last generation shell, $g_{(p)}$, comprises functional groups of formula:

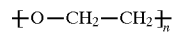

where $B_{(p)}$ and $M_{(p)}$, are defined analogously to B and M and where the 2 reactive groups of $M_{(p)}$ are connected to groups T in which T is a terminal group that is either H or halo, hydroxyl, amino, thiol, —O-tosyl, —O-mesyl, —O-tresyl, —O-brosyl, trifluoromethansulfonyl, aldehydo, carboxy, or an amido group, said terminal group T being free, either dissociated or undissociated, or protected by a protective group, or $M_{(p)}$ is a single bond, no branching exists and the last generation shell $g_{(p)}$ is formed by groups of formula:

where $B_{(p)}$ and T are as above defined, and (c) when p=1, the macromolecule contains only one generation shell, $g_{(p)}$, which corresponds to $g_{(1)}$ and has the formula:

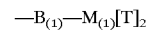

where $B_{(1)}$ and $M_{(1)}$ are defined analogously to $B_{(p)}$ and $M_{(p)}$ and T is as above defined.

As a consequence, in this case the macromolecule is represented by the following formula:

$A[g_{(1)}]_r$, i.e.

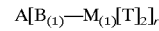

in which A, $B_{(1)}$, $M_{(1)}$, T, and r are defined as above.

Compounds of formula (I) also comprise the ones which are labelled with isotopes such as $^{13}C$, $^{14}C$, $^{2}H$, $^{3}H$, and $^{125}I$.

For seek of clarity a schematic representation of the structure of the macromolecules of the present invention is sequentially developed according to the following series of formulae:

  (I), where:

$G_{(1 \to p)}$ represents $B_{(1)}$—$M_{(1)}[G_{(2 \to p)}]_2$, in which $B_{(1)}$—$M_{(1)}$ is $g_{(1)}$ and $G_{(2 \to p)}$ represents $B_{(2)}$—$M_{(2)}[G_{(3 \to p)}]_2$, in which $B_{(2)}$—$M_{(2)}$ is $g_{(2)}$ and so on until the last generation is reached in which $G_{(p)}$ represents $B_{(p)}$—$M_{(p)}[T]_2$ or $B_{(p)}$—[T], where the symbols used are as above defined.

The above development can be illustrated in complete form by the following expanded formula (II)

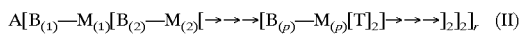  (II)

Compounds of the present invention which are particularly preferred are those in which r is 4 and in particular those in which the core A is a neopentyl residue of formula

Equally preferred are those in which B is a polyoxaethylene chain of formula

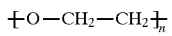

in which n is an integer from 0 to 20, preferably from 0 to 15 provided that in at least one generation shell n is other than 0.

Also preferred are those in which M is a bifunctional branching point represented by a group of formula:

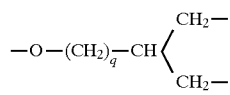

in which q=0.

Preferred macromolecular compounds are those in which the total. number of generation shells ranges from 1 to 20, preferably from 1 to 15.

Another example of preferred classes of compounds is represented by those having the following formula (III)

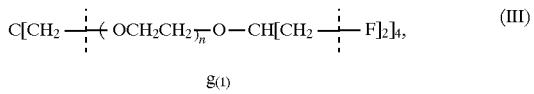  (III)

in which:
n is an integer from 0 to 20, preferably from 0 to 15, provided that in at least one generation shell n is other than 0,
$g_{(1)}$ is the first generation shell,
F is T, or the sequence of successive generation shells from $g_{(2)}$ to $g_{(p)}$, in which the last generation shell, $g_{(p)}$, comprises groups of formula —$(OCH_2CH_2)_n$—$OCH[CH_2-T]_2$ or groups of formula —$(OCH_2CH_2)_n$—T and T is as above defined,
moreover the total number of generation shells p can be as high as 20, preferably 15.

The present invention is illustrated through the preparation of macromolecules having a neopentyl core from which four polyoxaethylene chains depart. The binary branching is obtained through the introduction of a residue of glycerol on the terminal functions of said polyoxaethylene chains. The synthesis of the compounds of the present invention can preferably be performed by two independent synthetic processes:

a) lengthening of the polyoxaethylene chain, b) branching.

The order of these synthetic pathways can be modulated at will, in particular with regard to the type of compound and reaction conditions employed. It is possible to decide to begin with the central nucleus and successively add the polyoxaethylene chains of the first generation, the branching points, the polyoxaethylene chains of the second generation, the new branching points and so on until the desired number of generation shell has been reached.

Alternatively, it is equally possible to previously prepare branched polyoxaethylene chains (repetition units) and then to attach these to either the central nucleus, so forming the first generation, or to a previously formed generation shell.

Obviously, just as it is possible to use one or the other of the two synthetic processes, it is also possible to follow in part the first process and in part the second one (mixed procedure) according to the synthetic problem to overcome. The reactive functions not involved in a specific reaction are previously protected with suitable protective groups according to methods well known to the skilled technician. A consequence of this is that also the processes of preparation of these macromolecular compounds are an embodiment of the present invention.

An illustrative view of preferred synthetic pathways is disclosed in the following experimental section.

For all the described compounds, analytical data such as elemental analysis, $^{1}H$ and $^{13}C$ NMR and mass analysis resulted in agreement with the desired structures.

EXAMPLE 1

Synthesis of 2-phenyl-1,3-dioxa-5-cyclohexanol (cis, trans)

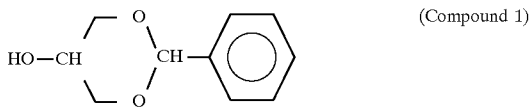

(Compound 1)

Benzaldehyde (0.8 mol) and glycerol (0.75 mol) were dissolved in benzene (150 mL) and p-toluensulfonic acid (0.0053 mol) was added to the solution. The reaction mixture was warmed and kept at 105° C. until 90% of the theoretical amount of water (12 mL) was distilled and then the reaction temperature was cooled down to room temperature and $NaHCO_3$ (0.0053 mol) was added to neutralize the p-toluensulfonic acid. The solvent was evaporated under reduced pressure and the oily residue was taken up with petroleum ether (300 mL) and stored at −15° C. overnight. The white precipitate was filtered and recrystallized from a mixture of benzene/petroleum ether 1/1 (v/v) (300 mL). The white solid consisted of a mixture of two product by TLC (isomer cis and trans) which were separated by column chromatography using a mixture of EtOAc/n-esane 70/30 (v/v). The chromatographyc fraction containing the products were combined and concentrated under reduced pressure to give the two different isomers. Yield 30% (cis) and 20% (trans). Both the cis and the trans isomer were used as branching units.

EXAMPLE 2

Synthesis of 1,15-bis[(1,3-dioxa-2-phenyl-5-cyclohexyl)oxy]-8,8-bis[7-((1,3-dioxa-2-phenyl-5-cyclohexyl)oxy)-2,5-dioxaheptyl]-3,6,10,13-tetraoxapentadecane

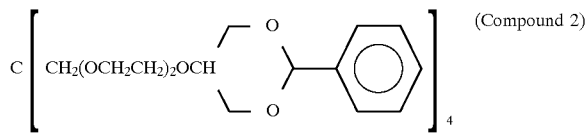

(Compound 2)

KOH (0.010 mol) was suspended in DMSO (5 mL) and 2-phenyl-1,3-dioxa-5-cyclohexanol (isomer cis; 0.01 mol) dissolved in DMSO (8 mL) was added. The reaction mixture was stirred for 3 h at room temperature then 1,15-bis(p-toluensulfonyloxy)-8,8-bis[7-(p-toluensulfonyloxy)-2,5-dioxaheptyl]-3,6,10,13-tetraoxapentadecane (0.00216 mol), obtained as described in Example 4 of WO 95/25763, dissolved in DMSO (16 mL) was added and the mixture was stirred for 4 h at 30° C. After this period the solvent was distilled under reduced pressure and the residue was taken up with water (50 mL) and extracted with $CH_2Cl_2$ (50 mL×4). The organic layer were combined and dried over $Na_2SO_4$, filtered and concentrated under reduced pressure. The crude product was purified by column chromatography using a mixture of EtOAc/acetone 85/15 (v/v). The chromatographic fraction containing the product were combined and concentrated under reduced pressure to give 1,15-bis[(2-phenyl-1,3-dioxa-5-cyclohexyl)oxy]-8,8-bis[7-((2-phenyl-1,3-dioxa-5-cyclohexyl)oxy)-2,5-dioxaheptyl]-3,6,10,13-tetraoxapentadecane (isomer cis) as a white oil (0.001 mol). Yield 45%. The trans isomer was obtained starting from the corresponding trans cyclohexanol derivative.

EXAMPLE 3

Synthesis of 2,20-dihydroxymethyl-11,11-bis[9-(hydroxylmethyl)-2,5,8-trioxa-10-hydroxy decyl]-3,6,9,13,16,19-hexaoxaenicosan-1,21-diol

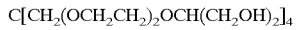

C[CH$_2$(OCH$_2$CH$_2$)$_2$OCH(CH$_2$OH)$_2$]$_4$  (Compound 3)

Compound 2 (cis isomer) was dissolved in MeOH (10 mL) and 6N HCl (1 mL) was added to the solution. After 4 h at room temperature NaHCO$_3$ was added to neutral pH, the inorganic salts were filtered off and the organic layer dried over Na$_2$SO$_4$, filtered and evaporated under vacuum. The crude product was purified by silica column chromatography using CH$_3$CN/H$_2$O 75/25 as eluent. Yield 50%. The same product was also obtained starting from the trans isomer.

EXAMPLE 4

Synthesis of 1,27-bis[(1,3-dioxa-2-phenyl-5-cyclohexyl)oxy]-14,14-bis[13-((1,3-dioxa-2-phenyl-5-cyclohexyl)oxy)-2,5,8,11-tetraoxatridecyl]-3,6,9,12,16,19,22,25-octaoxaheptacosane

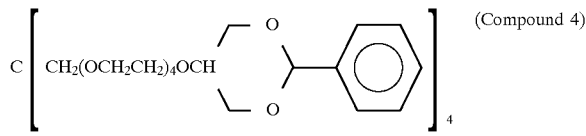

(Compound 4)

Compound 4 was obtained starting from the compound 1,28-bis(p-toluensulfonyloxy)-14,14-bis[13-(p-toluensulfonyloxy)-2,5,8,11-tetradecyl]-3,6,9,12,16,19,22,25-octaoxaheptacosane, obtained as described in Example 4 of WO 95/25763 and compound 1, described in Example 1, following the procedure described in Example 2. The crude product was purified by silica gel column chromatography using a mixture of EtOAc/acetone 7/3 as eluent. Yield 45%.

EXAMPLE 5

Synthesis of 2,32-hydroxymethyl-17,17-bis[16-hydroxy-15-(hydroxymethyl)-2,5,8,11,14-pentaoxahexadccyl]-3,6,9,12,15,19,22,25,28,31-decaoxatritriacontan-1,33-diol

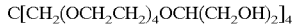

C[CH$_2$(OCH$_2$CH$_2$)$_4$OCH(CH$_2$OH)$_2$]$_4$  (Compound 5)

Compound 4 was deprotected by acid hydrolysis with 6N HCl and following the procedure described in Example 3. The pure product was obtained after column chromatography using CH$_3$CH/H$_2$O 7/3 as eluent. Yield 50%.

EXAMPLE 6

Synthesis of 1,33-bis(oxan-2-yl-oxy)-8,26-bis[7-(oxan-2-yl-oxy)-2,5-dioxaheptyl]-17,17-bis[16-(oxan-2-yl-oxy)-9-(7-(oxan-2-yl-oxy)-2,5-dioxaheptyl)-2,5,8,11,14-pentaoxahexadecyl]-3,6,9,12,15,19,22,25,28,31-decaoxatritriacontane (Compound 6)

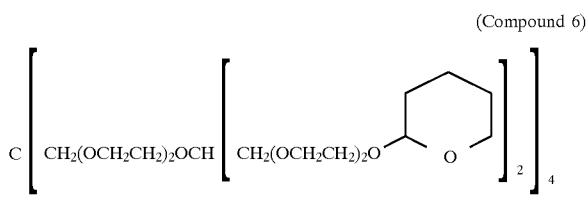

Compound 5 (0.0017 mol) was suspended in 19M NaOH (0.14 mol), the suspension was warmed at 65° C. under nitrogen and vigorous mechanical stirring for 1 h. 2-(3-oxa-5-chloropentyloxy)oxane, prepared as described in Example 1 of WO 95/25763, (0.02 mol) and tetrabutylammoniumhydrogen sulfate (TBAHS) (0.0007 mol) were added to the mixture. After 96 h at 65° C. an identical amount of 19M NaOH, 2-(3-oxa-5-chloropentyloxy)oxane and TBAHS were added and the reaction mixture was reacted for 72 h at 65° C. The reaction was monitored by MALDI-TOF and, if necessary, 19M NaOH (0.07 mol), 2-(3-oxa-5-chloropentyloxy)oxane (0.01 mol) and TBAHS (0.00035 mol) were added. At the end of reaction the temperature was cooled down to room temperature and the reaction mixture was diluted with water and extracted with diethyl ether. The organic layers were combined, dried over Na$_2$SO$_4$, filtered and evaporated under reduced pressure. The crude product was purified by silica column chromatography using AcOEt/acetone 6/4 as eluent. Yield 75%.

EXAMPLE 7

Synthesis of 8,26-bis(2,5-dioxa-7-hydroxyheptyl)-17,17-bis[9-(2,5-dioxa-7-hydroxyheptyl)-2,5,8,11,14-pentaoxa-16-hydroxyhexadecyl]-3,6,9,12,15,19,22,25,28,31-decaoxatritriacontan-1,33-diol

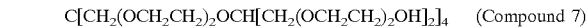

C[CH$_2$(OCH$_2$CH$_2$)$_2$OCH[CH$_2$(OCH$_2$CH$_2$)$_2$OH]$_2$]$_4$  (Compound 7)

Compound 6 (0.0012 mol) was dissolved in CH$_2$Cl$_2$/MeOH 1/1 by vol. (30 mL) and 37% HCl (1 mL) was added to the solution. After 14 h at room temperature NaHCO$_3$ was added to neutral pH the inorganic salts were filtered off and the organic layer dried over Na$_2$SO$_4$, filtered and evaporated under vacuum. The crude product was purified by silica column chromatography using CH$_3$CN/H$_2$O 70/30 as eluent. Yield 70%.

EXAMPLE 8

Synthesis of 1,45-bis(oxan-2-yl-oxy)-8,38-bis[7-(oxan-2-yl-oxy)-2,5-dioxaheptyl]-23,23-bis[22-(oxan-2-yl-oxy)-15-

(7-(oxan-2-yl-oxy)-2,5-fioxaheptyl)-2,5,8,11,14,17,20-heptaoxadocosyl]-3,6,9,12,15,18,21,25,28,31,34,37,40,43-tetradecaoxapentatetracontane (Compound 8)

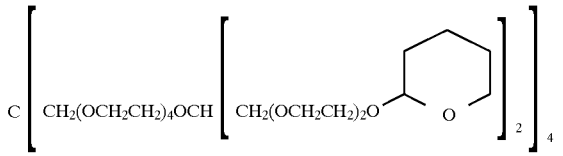

Compound 8 was obtained starting from compound 5 described in Example 5 following the procedure described in Example 6. The purified product was obtained after purification by column chromatography using a mixture of EtOAc/acetone as eluent. Yield 70%.

EXAMPLE 9

Synthesis of 8,38-bis(2,5-dioxa-7-hydroxyheptyl)-23,23-bis[15-(2,5-dioxa-7-hydroxyheptyl)-2,5,8,11,14,17,20-heptaoxa-22-hydroxydocosyl]-3,6,9,12,15,18,21,25,28,31,34,37,40,43-tetradecaoxapentatetracontan-1,45-diol C[CH₂(OCH₂CH₂)₄OCH[CH₂(OCH₂CH₂)₂OH]₂]₄  (Compound 9)

Compound 8 was deprotected following the procedure described in Example 7. The crude product was purified by column chromatography to give compound 9. Yield 80%.

EXAMPLE 10

Synthesis of 1,57-bis(oxan-2-yl-oxy)-14,44-bis[13-(oxan-2-yl-oxy)-2,5,8,11-tetraoxatridecyl]-29,29-bis[28-(oxan-2-yl-oxy)-15-(13-(oxan-2-yl-oxy)-2,5,8,11-tetraoxatridecyl)-2,5,8,11,14,17,20,23,26-nonaoxaoctacosyl]-3,6,9,12,15,18,21,24,27,31,34,37,40,43,46,49,52,55-octadecaoxaheptapentacontane (Compound 10)

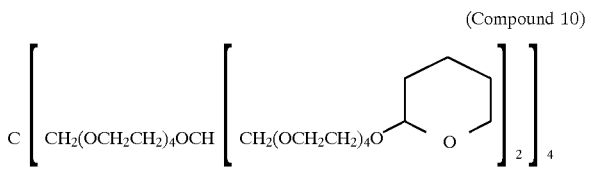

Compound 10 was obtained starting from compound 9 described in Example 9 following the procedure described in Example 6. The product was obtained after purification by silica gel column chromatography using a mixture of EtOAc/acetone as eluent. Yield 60%.

EXAMPLE 11

Synthesis of 14,44-bis(2,5,8,11-tetraoxa-13-hydroxytridecyl)-29,29-bis[15-(2,5,8,11-tetraoxa-13-hydroxytridecyl)-2,5,8,11,14,17,20,23,26-nonaoxa-28-hydroxyoctacosyl]-3,6,9,12,15,18,21,24,27,31,34,37,40,43,46,49,52,55-octadecaoxaheptapentacontan-1,57-diol (Compound 11)

Compound 11 was obtained by acid hydrolysis of the compound 10 described in Example 10, following the procedure described in Example 7. Yield 85%.

EXAMPLE 12

Synthesis of 1,69-bis(oxan-2-yl-oxy)-20,50-bis[19-(oxan-2-yl-oxy)-2,5,8,11,14,17-hexaoxanonadecyl]-35,35-bis[34-(oxan-2-yl-oxy)-15-(19-(oxan-2-yl-oxy)-2,5,8,11,14,17-hexaoxanonadecyl)-2,5,8,11,14,17,20,23,26,29,32-undccaoxatetratriacontyl]-3,6,9,12,15,18,21,24,27,30,33,37,40,43,46,49,52,55,58,61,64,67-docosaoxanonahexacontane (Compound 12)

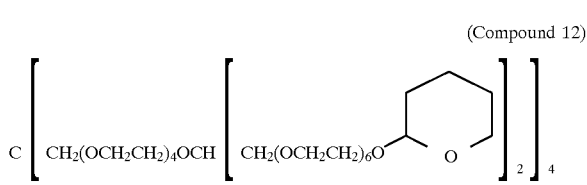

Compound 12 was obtained starting from compound 11 following the procedure described in Example 6. The crude product was purified by column chromatography using a mixture of EtOAc/acetone as eluent. Yield 50%.

EXAMPLE 13

Synthesis of 20,50-bis(2,5,8,11,14,17-hexaoxa-19-hydroxynonadecyl)-35,35-bis[15-(2,5,8,11,14,17-hexaoxa-19-hydroxynonadecyl)-2,5,8,11,14,17,20,23,26,29,32-undecaoxa-34-hydroxytetratriacontyl]-3,6,9,12,15,18,21,24,27,30,33,37,40,43,46,49,52,55,58,61,64,67-docosaoxanonahexacontan-1,69-diol (Compound 13)

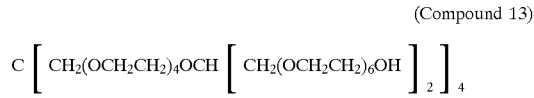

Compound 12 was deprotected by acid hydrolysis of the compound described in Example 12, following the procedure described in Example 7. Yield 80%.

EXAMPLE 14

Synthesis of 1,33-bis(p-toluensulfonyloxy)-8,26-bis[7(p-toluensulfonyloxy)-2,5-dioxaheptyl]-17,17-bis[16-(p-toluensulfonloxy)-9-(7(p-toluensulfonyloxy)-2,5-dioxaheptyl)-2,5,8,11,14-pentaoxahexadecyl]-3,6,9,12,15,19,22,25,28,31-decaoxatritriacontane (Compound 14)

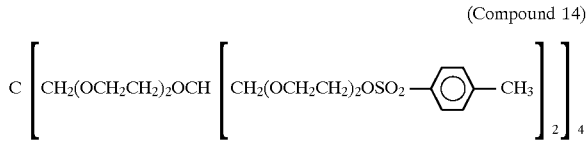

p-Toluensulfonylchloride (0.013 mol) was dissolved in CH₂Cl₂ (25 mL) and triethylamine (TEA) (0.0142 mol) was added to the solution. The reaction temperature was cooled down to −10° C. and then compound 6 (0.0013 mol) dissolved in CH₂Cl₂ (25 mL) was dropped to the solution. After 4 days the reaction was not complete and a further amount of p-toiuensulfonylchloride (0.0065 mol) dissolved in CH₂Cl₂ (25 mL) and TEA (0.007 mol) were added to the mixture. At the end of reaction the mixture was washed with water (3×100 mL), the organic layer was dried over Na₂SO₄ filtered and concentrated under reduced pressure. The crude product was purified by silica column chromatography using AcOEt/acetone 85/15 as eluent. Yield 65%.

EXAMPLE 15

Synthesis of 1,57-bis(p-toluensulfonyloxy)-14,44-bis[13-(p-toluensulfonyloxy)-2,5,8,11-tetraoxatridecyl]-29,29-bis[28-(p-toluensulfonyloxy)-15-(13-(p-toluensulfonyloxy)-2,5,8,11-tetraoxatridecyl)-2,5,8,11,14,17,20,23,26- nonaoxaoctacosyl]-3,6,9,12,15,18,21,24,27,31,34,37,40,43,46,49,52,55-octadecaoxaheptapentacontane (Compound 15)

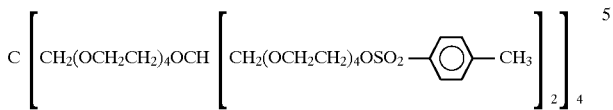

Compound 15 was obtained starting from compound 11 following the procedure described in Example 14. The crude products purified by column chromatography using EtOAc/acetone as eluent. Yield 60%.

EXAMPLE 16

Synthesis of 1,69-bis(p-toluensulfonyloxy)-20,50-bis[19-(p-toluensulfonyloxy)-2,5,8,11,14,17-hexaoxanonadecyl]-35,35-bis[34-(p-toluensulfonyloxy)-15-(19-(p-toluensulfonyloxy)-2,5,8,11,14,17-hexaoxanonadecyl)-2,5,8,11,14,17,20,23,26,29,32-undecaoxatetratriacontyl]-3,6,9,12,15,18,2 1,24,27,30,33,37,40,43,46,49,52,55,58,61,64,67-docosaoxanonahexacontane (Compound 16)

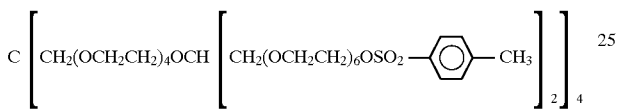

Compound 16 was obtained starting from compound 13 and following the procedure described in Example 14. The crude product was purified by column chromatography using EtOAc/acetone as eluent.

EXAMPLE 17

Synthesis of 1,69-diphthalimido-20,50-bis[19-phthalimido-2,5,8,11,14,17-hexaoxanonadecyl]-35,35-bis[34-phthalimido-15-(19-phthalimido-2,5,8,11,14,17-hexaoxanonadecyl)-2,5,8,11,14,17,20,23,26,29,32-undecaoxatetratriacontyl]-3,6,9,12,15,18,2 1,24,27,30,33, 37,40,43,46,49,52,55,58,61,64,67-docosaoxanonahexacontane (Compound 17)

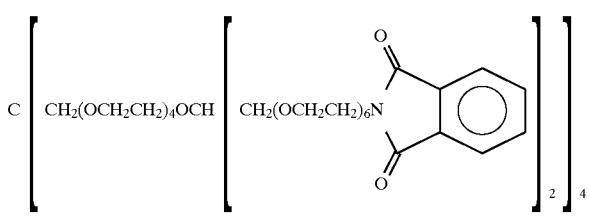

Compound 17 was obtained starting from compound 16 and potassium phthalimide in DMF at 140 ° C. The crude product was purified by silica gel column using EtOAc/acetone as eluent. Yield 40%.

EXAMPLE 18

Synthesis of 1,69-diamino-20,50-bis(19-amino-2,5,8,11,14,17-hexaoxanonadecyl)-35,35-bis[34-amino-15-(19-amino-2,5,8,11,14,17-hexaoxanonadecyl)-2,5,8,11,14,17,20,23,26,29,32-undecaoxatetratriacontyl]-3,6,9,12,15,18,21,24,27,30,33,37,40,43,46,49,52,55,58,61,64,67-docosaoxanonahexacontane (Compound 18)

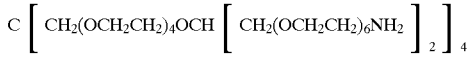

Compound 18 was obtained starting from compound 17, obtained as described in Example 17, and hydrazine in EtOH at reflux. Yield

EXAMPLE 19

Synthesis of 1,33-bis(1,3-dioxa-2-phenyl-5-cyclohexyioxy)-8,26-bis[7-(1,3-dioxa-2-phenyl-5-cyclohexyloxy)-2,5-dioxaheptyl]-17,17-bis[16-(1,3-dioxa-2-phenyl-5-cyclohexyloxy)-9-[(7-(1,3-dioxa-2-phenyl-5-cyclohexyloxy)-2,5-dioxaheptyl)-2,5,8,11,14-pentaoxahexadecyl]-3,6,9,12,15,19,22,25,28,31-decaoxatritiacontane (Compound 19)

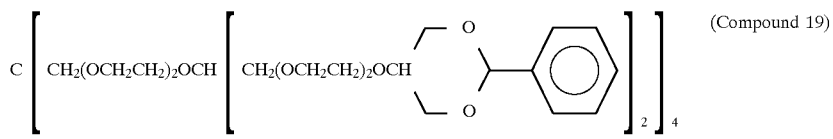

Compound 19 was obtained starting from compound 14 described in Example 14 by reaction with compound 1 described in Example 1 (either in cis or trans form) following the procedure described in Example 2. After reaction the product was purified by silica gel column chromatography using a mixture of EtOAc/acetone 7/3 vol. Yield 40%.

EXAMPLE 20

Synthesis of 2,38-bis(hydroxymethyl)-11,29-bis[9-(hydroxymethyl)-2,5,8-trioxa-10-hydroxydecyl]-20,20-bis[18-(hydroxymethyl)-9-(9-(hydroxymethyl)-2,5,8-trioxa-10-hydroxydecyl)-2,5,8,11,14,17-hexaoxa-19-hydroxynonadecyl]-3,6,9,12,15,18,22,25,28,3 1,34,37-dodecaoxanonatriacontan-1,39-diol (Compound 20)

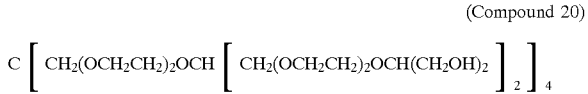

Compound 19 was dissolved in MeOH and treated with 6N HCl as described in Example 3. The product was purified by column chromatography essentially as described in Example 3. Yield 50%.

EXAMPLE 21

Synthesis of 1,57-bis(1,3-dioxa-2-phenyl-5-cyclohexyloxy)-14,44-bis[13-(1,3-dioxa-2-phenyl-5-cyclohexyloxy)-2,5,8,11-tetraoxatridecyl]-29,29-bis[(28-(1,3-dioxa-2-phenyl-5-cyclohexyloxy)-15-(13-(1,3-dioxa-2- phenyl-5-cyclohexyloxy)-2,5,8,11-tetraoxatridccyl)-2,5,8,11,14,17,20,23,26-nonaoxaoctacosyl]-3,6,9,12,15,18,21,24,27,31,34,37,40,43,46,49,52,55-octadecaoxaheptapcntacontane

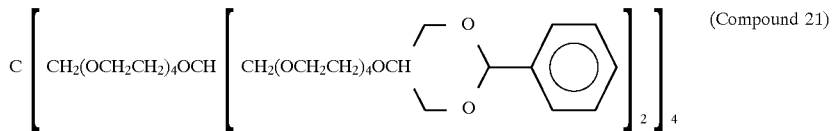
(Compound 21)

Compound 21 was obtained starting from compound 15 described in Example 15 and compound 1, described in Example 1, following the procedure described in Example 2. The product was purified by column chromatography using a mixture of EtOAc/acetone. Yield 35%.

EXAMPLE 22

Synthesis of 2,62-bis(hydroxymethyl)-17,47-bis[15-(hydroxymethyl)-2,5,8,11,14-pentaoxa-16-hydroxyhexadecyl]-32,32-bis[30-(hydroxymethyl)-15-(15-(hydroxymethyl)-2,5,8,11,14-pentaoxa-16-hydroxyhexadecyl)-2,5,8,11,14,17,20,23,26,29-decaoxa-31-hydroxyhentriacontyl]-3,6,9,12,15,18,21,24,27,30,34,37,40,43,46,49,52,55,58,61-icosaoxatrihexacontan-1,63-diol

(Compound 22)

Compound 21 was dissolved in MeOH and treated with 6N HCl as described in Example 3. The product was purified by column chromatography essentially as described in Example 3. Yield 50%.

EXAMPLE 23

Synthesis of 1,51-bis(oxan-2-yl-oxy)-26,26-bis[25-(oxan-2-yl-oxy)-9-[16-(oxan-2-yl-oxy)-9-(7-(oxan-2-yl-oxy)-2,5-dioxaheptyl)-2,5,8,11,14-pentaoxahexadecyl]-2,5,8,11,14,17,20,23-octaoxapentacosyl]-17,35-bis[16-(oxan-2-yl-oxy)-9-(7-(oxan-2-yl-oxy)-2,5-dioxaheptyl)-2,5,8,11,14-pentaoxahexadecyl]-8,44-bis[7-(oxan-2-yl-oxy)-2,5-dioxaheptyl]-3,6,9,12,15,18,21,24,28,31,34,37,40,43,46,49-hexadecaoxahenpentacontane

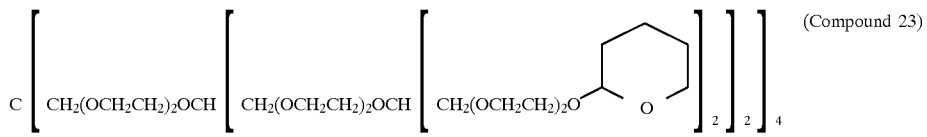
(Compound 23)

Compound 23 was obtained starting from compound 20 described in Example 20 following the procedure described in Example 6. The product was obtained after purification by silica gel column chromatography using a mixture of EtOAc/acetone as eluent. Yield 50%.

EXAMPLE 24

Synthesis of 26,26-bis[9-(9-(2,5-dioxa-7-hydroxyheptyl)-2,5,8,11,14-pentaoxa-16-hydroxyhexadecyl)-2,5,8,11,14,17,20,23-octaoxa-25-hydroxypentacosyl]-17,35-bis[9-(2,5-dioxa-7-hydroxyheptyl)-2,5,8,11,14-pentaoxa-16-hydroxyhexadecyl]-8,44-bis(2,5-dioxa-7-hydroxyheptyl)-3,6,9,12,15,18,21,24,28,31,34,37,40,43,46,49-hexadecaoxahenpentacontan-1,51-doil

(Compound 24)

Compound 24 was obtained by acid hydrolysis of compound 23, following the procedure described in Example 7. Yield 85%.

EXAMPLE 25

Synthesis of 1,75-bis(oxan-2-yl-oxy)-38,38-bis[37-(oxan-2-yl-oxy)-15-[22-(oxan-2-yl-oxy)-15-[7-(oxan-2-yl-oxy)-2,5-dioxaheptyl)-2,5,8,11,14,17,20-heptaoxadocosyl]-2,5,8,11,14,17,20,23,26,29,32,35-dodecaoxaheptatriacontyl]-23,53-bis[22-(oxan-2-yl-oxy)-15-(7-(oxan-2-yl-oxy)-2,5-dioxaheptyl)-2,5,8,11,14,17,20-heptaoxadocosyl]-8,68-bis[7-(oxan-2-yl-oxy)-2,5-dioxaheptyl]-3,6,9,12,15,18,21,24,27,30,33,36,40,43,46,49,52,55,58,61,64,67,70,73-tetracosaoxapentaheptacontane

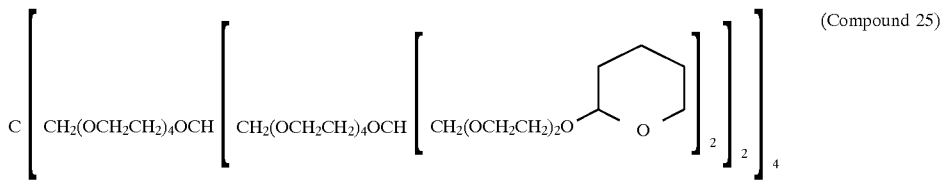
(Compound 25)

Compound 25 was obtained starting from compound 22 described in Example 22 following the procedure described in Example 6. The product was obtained after purification by silica gel column chromatography using a mixture of EtOAc/acetone as eluent. Yield 50%.

EXAMPLE 26

Synthesis of 38,38-bis[15-(15-(2,5-dioxa-7-hydroxyheptyl)-2,5,8,11,14,17,20-heptaoxa-22-hydroxydocosyl)-2,5,8,11,14,17,20,23,26,29,32,35-dodecaoxa-37-hydroxyheptatriacontyl]-23,53-bis[15-(2,5-dioxa-7-hydroxyheptyl)-2,5,8,11,14,17,20-heptaoxa-22-hydroxydocosyl]-8,68-bis(2,5-dioxa-7-hydroxyheptyl)-3,6,9,12,15,18,21,24,27,30,33,36,40,43,46,49,52,55,58,61,64,67,70,73-tetracosaoxapentaheptacontan-1,75-diol

(Compound 26)

Compound 26 was obtained by acid hydrolysis of compound 25, following the procedure described in Example 7. Yield 85%.

EXAMPLE 27

Synthesis of 1,87-bis(oxan-2-yl-oxy)-44,44-bis[43-(oxan-2-yl-oxy)-15-[28-(oxan-2-yl-oxy)-15-(13-(oxan-2-yl-oxy)-2,5,8,11-tetraoxatridecyl)-2,5,8,11,14,17,20,23,26-nonaoxaoctacosyl]-2,5,8,11,14,17,20,23,26,29,32,35,38,41-tetradecaoxatritriacontyl]-29,59-bis[28-(oxan-2-yl-oxy)-15-[13-(oxan-2-yl-oxy)-2,5,8,11-tetraoxatridecyl]-2,5,8,11,14,17,20,23,26-nonaoxaoctacosyl]-14,74-bis[13-(oxan-2-yl-oxy)-2,5,8,11-tetraoxatridecyl]-3,6,9,12,15,18,21,24,27,30,33,36,39,42,46,49,52,55,58,61,64,67,70,73,76,79,82,85-octacosaoxaheptaoctacontane column chromatography using a mixture of EtOAc/acetone as eluent. Yield 45%.

EXAMPLE 28

Synthesis of 44,44-bis[15-(15-(2,5,8,11-tetraoxa-13-hydroxytridecyl)-2,5,8,11,14,17,20,23,26-nonaoxa-28-hydroxyoctacosyl)-2,5,8,11,14,17,20,23,26,29,32,35,38,41-tetradecaoxa-43-hydroxytritetracontyl]-29,59-bis[15-(2,5,8,11-tetraoxa-13-hydroxytridecyl)-2,5,8,11,14,17,20,23,26-nonaoxa-28-hydroxyoctacosyl]-3,6,9,12,15,18,21,24,27,30,33,36,39,42,46,49,52,55,58,61,64,67,70,73,76,79,82,85-octacosaoxaheptaoctacontan-1,87-diol

(Compound 28)

Compound 28 was obtained by acid hydrolysis of compound 27, following the procedure described in Example 7. Yield 85%.

EXAMPLE 29

Synthesis of 1,51-bis(p-toluensulfonyloxy)-26,26-bis[25-(p-toluensulfonyloxy)-9-[16-(p-toluensulfonyloxy)-9-(7-(p-toluensulfonyloxy)-2,5-dioxaheptyl)-2,5,8,11,14-pentaoxahexadecyl]-2,5,8,11,14,17,20,23-octaoxapentacosyl]-17,35-bis[16-(p-toluensulfonyloxy)-9-(7-(p-toluensulfonyloxy)-2,5-dioxaheptyl)-2,5,8,11,14-pentaoxahexadecyl]-8,44-bis[7-(p-toluensulfonyloxy)-2,5-dioxaheptyl]-3,6,9,12,15,18,21,24,28,31,34,37,40,43,46,49-hexadecaoxahenpentacontane

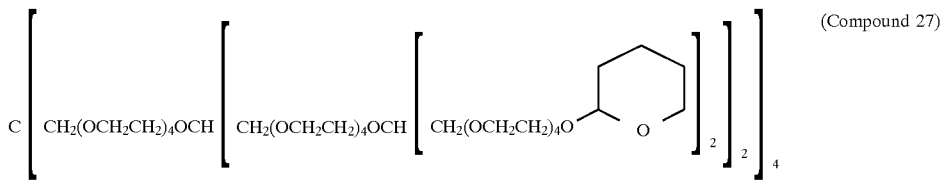
(Compound 27)

The product was obtained starting from the compound 26 described in Example 26 following the procedure described in Example 6. The pure product was obtained after silica gel

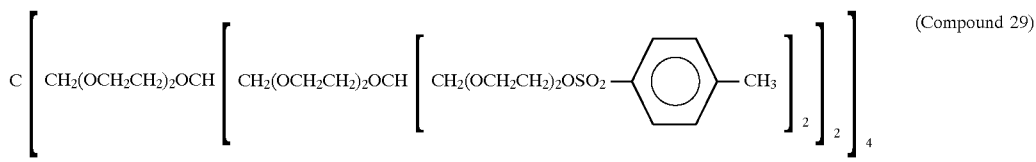
(Compound 29)

Compound 29 was obtained starting from compound 24 following the procedure described in Example 14. The crude product was purified by column chromatography using EtOAc/acetone as eluent. Yield 50%.

EXAMPLE 30

Synthesis of 1,87-bis(p-toluensulfonyloxy)-44,44-bis[43-(p-toluensulfonyloxy)-15-[28-(p-toluensulfonyloxy)-15-(13-(p-toluensulfonyloxy)-2,5,8,11-tetraoxatridecyl)-2,5,8,11,14,17,20,23,26-nonaoxaoctacosyl]-2,5,8,11,14,17,20,23,26,29,32,35,38,41-tetradecaoxatritriacontyl]-29,59-bis[28-(p-toluensulfonyloxy)-15-[13-(p-toluensulfonyloxy)-2,5,8,11-tetraoxatridecyl]-2,5,8,11,14,17,20,23,26-nonaoxaoctacosyl]-14,74-bis[13-(p-toluensulfonyloxy)-2,5,8,11-tetraoxatridecyl]-3,6,9,12,15,18,21,24,27,30,33,36,39,42,46,49,52,55,58,61,64,67,70,73,76,79,82,85-octacosaoxaheptaoctacontane

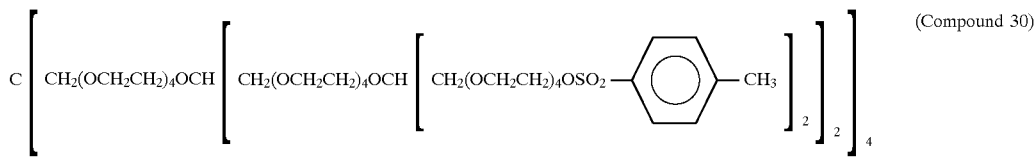
(Compound 30)

Compound 30 was obtained starting from compound 28 following the procedure described in Example 14. The crude product was purified by column chromatography using EtOAc/acetone as eluent. Yield 50%.

EXAMPLE 31

Synthesis of 1,51-bis(1,3-dioxa-2-phenyl-5-cyclohexyloxy)-26,26-bis[25-(1,3-dioxa-2-phenyl-5-cyclohexyloxy)-9-[16-(1,3-dioxa-2-phenyl-5-cyclohexyloxy)-9-(7-(1,3-dioxa-2-phenyl-5-cyclohexyloxy)-2,5-dioxaheptyl)-2,5,8,11,14-pentaoxahexadecyl]-2,5,8,11,14,17,20,23-octaoxapentacosyl]-17,35-bis[16-(1,3-dioxa-2-phenyl-5-cyclohexyloxy)-9-(7-(1,3-dioxa-2-phenyl-5-cyclohexyloxy)-2,5-dioxaheptyl)-2,5,8,11,14-pentaoxahexadecyl]-8,44-bis[7-(1,3-dioxa-2-phenyl-5-cyclohexyloxy)-2,5-dioxaheptyl]-3,6,9,12,15,18,21,24,28,31,34,37,40,43,46,49-hexadecaoxahenpentacontane The product was purified by column chromatography using a mixture of EtOAc/acetone. Yield 35%.

EXAMPLE 32

Synthesis of 2,56-bis(hydroxymethyl)-29,29-bis[27-(hydroxymethyl)-9-[9-(9-(hydroxymethyl)-2,5,8-trioxa-10-hydroxydecyl)-18-(hydroxymethyl)-2,5,8,11,14,17-hexaoxa-19-hydroxynonadecyl]-2,5,8,11,14,17,20,23,26-nonaoxa-28-hydroxyoctacosyl]-20,38-bis[9-(9-(hydroxymethyl)-2,5,8-trioxa-10-hydroxydecyl)-18-(hydroxymethyl)-2,5,8,11,14,17-hexaoxa-19-hydroxynonadecyl]-11,47-bis[9-(hydroxymethyl)-2,5,8-trioxa-10-hydroxydecyl]-3,6,9,12,15,18,21,24,27,31,34,37,40,43,46,49,52,55-octadecaoxaheptapentacontan-1,57-diol

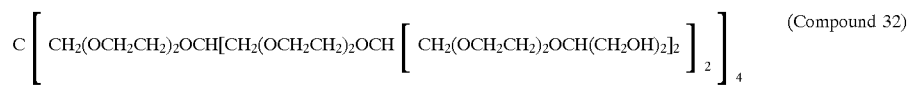
(Compound 32)

Compound 31 was dissolved in MeOH and treated with 6N HCl as described in Example 3. The product was purified by column chromatography essentially as described in Example 3. Yield 50%.

EXAMPLE 33

Synthesis of 1,87-bis(1,3-dioxa-2-phenyl-5-cyclohexyloxy)-44,44-bis[43-(1,3-dioxa-2-phenyl-5-cyclohexyloxy)-15-[28-(1,3-dioxa-2-phenyl-5-cyclohexyloxy)-15-(13-(1,3-dioxa-2-phenyl-5-cyclohexyloxy)-2,5,8,11-tetraoxatridecyl)-2,5,8,11,14,17,20,23,26-nonaoxaoctacosyl]-2,5,8,11,14,17,20,23,26,29,32,

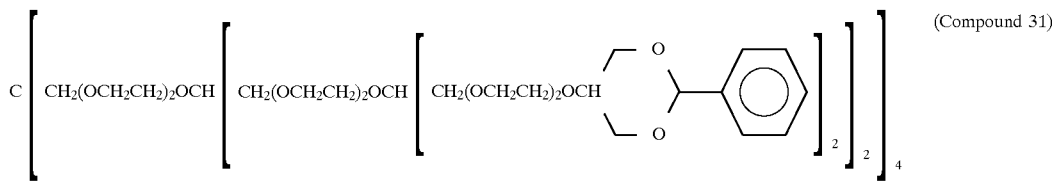
(Compound 31)

Compound 31 was obtained starting from compound 30, described in Example 30, and compound 1, described in Example 1, following the procedure described in Example 2.

35,38,41-tetradecaoxatritetracontyl]-29,59-bis[28-(1,3-dioxa-2-pheny-5-cyclohexyloxy)-15-(13-(1,3-dioxa-2-phenyl-5-cyclohexyloxy)-2,5,8,11-tetraoxatridecyl)-2,5,8,11,14,17,20,23,26-nonaoxaoctacosyl]-14,74-bis[13-(1,3- dioxa-2-phenyl-5-cyclohexyloxy)-2,5,8,11-tetraoxatridecyl]-3,6,9,12,15,18,21,24,27,30,33,36,39,42,46,49,52,55,58,61,64,67,70,73,76,79,82,85-octacosaoxaheptaoctacontane slowly and the reaction was stirred for 3 h at 50° C. After this period DMF was evaporated under reduced pressure, the residue was taken-up with water and extracted with $CH_2Cl_2$.

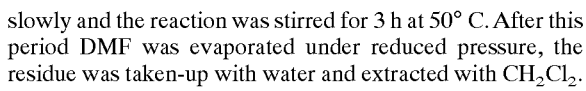
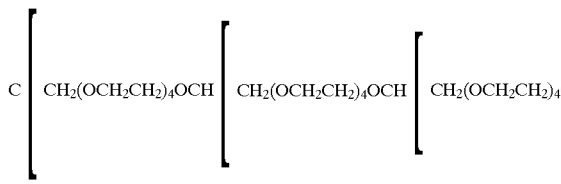
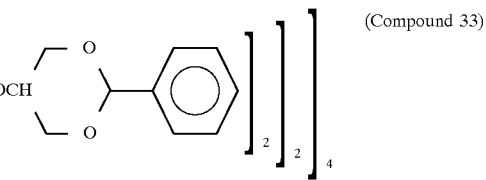

(Compound 33)

Compound 33 was obtained starting from compound 30 described in Example 30 and compound 1, described in Example 1, following the procedure described in Example 2. The product was purified by column chromatography using a mixture of EtOAc/acetone. Yield 35%.

The crude product was purified by silica gel column chromatography using EtOAc/MeOH as eluent. Yield 70%.

EXAMPLE 34

Synthesis of 2,92-bis(hydroxymethyl)47,47-bis[45-(hydroxymethyl)-15-[15-(15-(hydroxymethyl)-2,5,8,11,14-pentaoxa-16-hydroxyhexadecyl)-2,5,8,11,14,17,20,23,26,29-decaoxa-31-hydroxyhentriacontyl]-2,5,8,11,14,17,20,23,26,29,3 2,35,38,41,44-pentadecaoxa-46-hydroxyhexatetracontyl]-32,62-bis[15-(15-(hydroxymethyl)-2,5,8,11,14-pentaoxa-16-hydroxyhexadecyl)-2,5,8,11,14,17,20,23,26,29-decaoxa-31-hydroxyhentriacontyl]-17,77-bis[15-(hydroxymethyl)-2,5,8,11,14-pentaoxa-16-hydroxyhexadecyl]-3,6,9,12,15,18,21,24,27,30,33,36,39,42,45,49,52,55,58,61,64,67,70,73,76,79,82,83,88,91-triacontaoxatrinonacontan-1,93-diol

EXAMPLE 36

Synthesis of 1,87-(phthalimido)-44,44-bis[43-(phthalimido)-15-[28-(phthalimido)-15-(13-(phthalimido)-2,5,8,11-tetraoxatridecyl]-2,5,8,11,14,17,20,23,26-nonaoxaoctacosyl]30-[13-(phthalimido)-2,5,8,11-tetraoxatridecyl]-2,5,8,11,14,17,20,23,26,29,32,35,38,41-tetradecaoxatritetracontyl]-29,59-bis[28-(phthalimido)-15-(13-(phthalimido)-2,5,8,11-tetraoxatridecyl)-2,5,8,11,14,17,20,23,26-nonaoxaoctacosyl]-14,74-bis[13-(phthalimido)-2,5,8,11-tetraoxatridecyl]-3,6,9,12,15,18,21,24,27,30,33,36,39,42,46,49,52,55,58,61,64,67, 70,73,76,79,82,85,-octacosaoxaheptaoctacontane

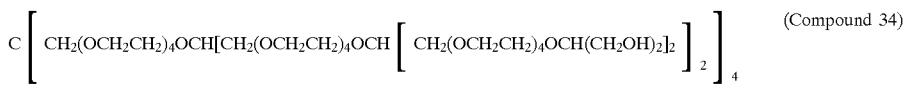

(Compound 34)

Compound 33 was dissolved in MeOH and treated with 6N HCl as described in Example 3. The product was purified by column chromatography essentially as described in Example 3. Yield 50%.

EXAMPLE 35

Synthesis of 1,87-dichloro-14,74-(13-chloro-2,5,8,11-tetraoxatrydecyl)-29,59-bis[28-chloro-15-(13-chloro-2,5,8,11-tetraoxatridecyl)-2,5,8,11,14,17,20,23,26-nonaoxaoctacosyl]44,44-bis[43-chloro-30-(13-chloro-2,5,8,11-tetraoxatridecyl)-5-[28-chloro-15-(13-chloro-2,5,8,11-tetraoxatridecyl)-2,5,8,11,14,17,20,23,26-nonaoxaoctacosyl]-2,5,8,11,14,17,20,23,26,2,32,35,38,41-tetradecaoxatritetracontyl]- 3,6,9,12,15,18,21,24,27,30,33,36,39,42,45,48,52,55,58,61,64,67,70,73,76,79,82,85-docooctaoxaoctaheptacontane.

Compound 35)

Compound 28 (0.017 mol) was dissolved in DMF and warmed at 50° C. Thionyl chloride (1,8 mol) was added (Compound 36)

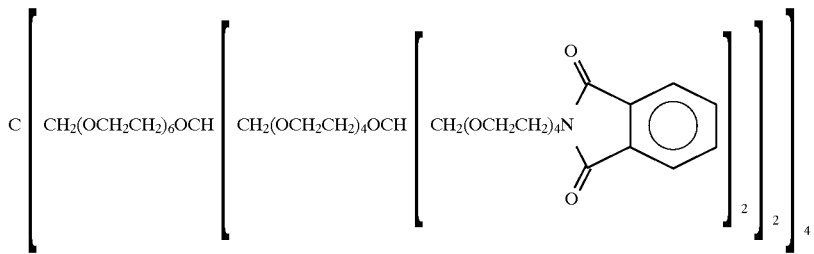

Compound 36 was obtained by reaction of compound 35, described in Example 35, and potassium phthalimide following the procedure described in Example 17. The crude product was purified by column chromatography using a mixture of EtOAc/MeOH as eluent. Yield 65%.

EXAMPLE 37

Synthesis of 1,45-bis(oxan-2-yl-oxy)-23,23-bis[22-(oxan-2-yl-oxy)-9-(13-(oxan-2-yl-oxy)-2,5,8,11-tetraoxatridecyl)-2,5,8,11,14,17,20-heptaoxaenicosyl]-14,32-bis[1 3-(oxan-2-yl-oxy)-2,5,8,11-tetraoxatridecyl]-3,6,9,12,15,18,21,25,28,31,34,37,40,43-tetradecaoxapentatetracontane (Compound 37)

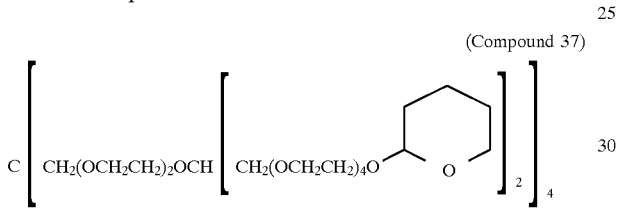

Compound 37 was obtained starting from compound 7, described in Example 7, following the procedure described in Example 6. The purified product was obtained after purification by column chromatography using a mixture of EtOAc/MeOH as eluent. Yield 75%.

EXAMPLE 38

Synthesis of 14,32-bis(2,5,8,11-tetraoxa-13-hydroxtridecyl)-23,23-bis[9-(2,5,8,11-tetraoxa-13-hydroxytridecyl)-2,5,8,11,14,17,20-heptaoxa-22-hydroxydocosyl]-3,6,9,12,15,18,21,25,28,31,34,37,40,43-tetradecaoxapentatetracontan-1,45-diol (Compound 38)

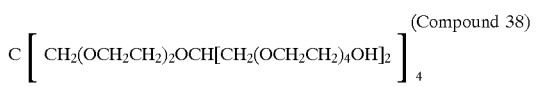

Compound 37 was deprotected following the procedure described in Example 7. The crude product was purified by column chromatography using a mixture of $CH_3CN/H_2O$ as eluent. Yield 85%.

EXAMPLE 39

Synthesis of 5-chloropentyl-3-oxa-p-toluensulphonate (Compound 39)

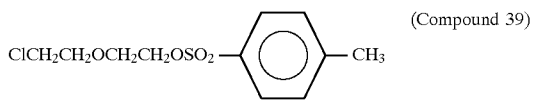

p-Toluensulphonylchloride (0.06 mol) was dissolved in $CH_2Cl_2$; the solution was cooled down to −2° C. and triethylamine (0.06 mol) was added. After 1 h 3-oxa-5-chloropentan-1-ol (0.040 mol) previously dissolved in $CH_2Cl_2$ was added. The cooling was interrupted and the reaction mixture was stirred at room temperature for 18 h. After this period the reaction was diluted and washed with water; the organic layer was dried and concentrated under reduced pressure. The crude product was purified by column chromatography using a mixture of petroleum benzine/EtOAc as eluent. Yield 85%.

EXAMPLE 40

Synthesis of 5-(5-chloro-3-oxapentyloxy)-2-phenyl-1,3-dioxacyclohexane (Compound 40)

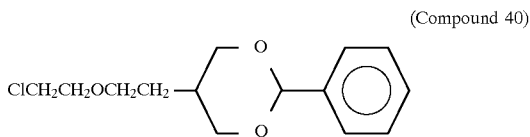

Compound 1, obtained as described in Example 1, (0.08 mol) was suspended in toluene and 19.06 mol NaOH (0.80 mol) was added to the suspension. The reaction mixture was warmed at 40° C. for 1 h and after this period tetrabutylammoniumbromide (0.008 mol) was added. After 30 minutes compound 39, obtained as described in Example 39, (0.07 mol) was added and the reaction was stirred for 72 h at 40° C. then was cooled down to room temperature, diluted with water and extracted with EtOAc. The organic layer was dried and evaporated under reduced pressure and the crude product was purified by column chromatography using a mixture of EtOAc/n-Hexane as eluent. Yield 75%.

EXAMPLE 41

Synthesis of 1,45-(1,3-dioxa-2-phenyl-5-cyclohexyloxy)-23,23-bis[22-(1,3-dioxa-2-phenyl-5-cyclohexyloxy)-9-(13-(1,3-dioxa-2-phenyl-5-cyclohexyloxy)-2,5,8,11-tetraoxatridecyl)-2,5,8,11,14,17,20-heptaoxadocosyl]-14,32-bis[13-(1,3-dioxa-2-phenyl-5-cyclohexyloxy)-2,5,8,11-tetraoxatridecyl]-3,6,9,12,15,18,21,25,28,31,34,37,40,43-tetradecaoxapentatetracontane

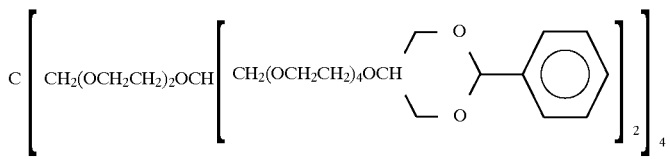
(Compound 41)

Compound 9, obtained as described in Example 9, (0.005 mol) was suspended in 19.06M NaOH (0.4 mol). The reaction mixture was stirred at 65° C. for 2 h then compound 40, obtained as described in Example 40, (0.065 mol) and tetrabutylammoniumbromide were added and the suspension was stirred at 65° C. for 22 h. Afterward 19.06M NaOH (0.2 mol), compound 40 (0.04 mol), tetrabutylammoniumbromide (0.001 mol) were added and after 15 h the reaction was cooled down to room temperature, diluted with water and extracted with $CH_2Cl_2$. The organic layer were combined, dried and concentrated under reduced pressure. The crude product was purified by column chromatography using a mixture of EtOAc/MeOH as eluent. Yield 70%

EXAMPLE 42

Synthesis of 2,50-bis(hydroxymethyl)-26,26-bis[24-(hydroxymethyl)-9-[15-(hydroxymethyl)-2,5,8,11,14-pentaoxa-16-hydroxyhexadecyl]-2,5,8,11,14,17,20,23-octaoxa-25-hydroxypentacosyl]-17,35-bis[15-(hydroxymethyl)-2,5,8,11,14-pentaoxa-16-hydroxyhexadecyl]-3,6,9,12,15,18,21,24,28,3 1,34,37,40,43,46,49-hexadecaoxahenpentacontan-1,51-diol.

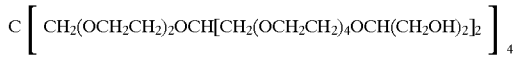
(Compound 42)

Compound 41, obtained as described in Example 41, (0.006 mol) was dissolved in a mixture of $H_2O$, MeOH and 37% HCl. The solution was stirred at room temperature for 72 h, then $NaHCO_3$ was added to neutral pH, the salts were filtered off and the solvent was evaporated under reduced pressure. The crude product was purified by column chromatography using a mixture of $CH_3CN/H_2O$ as eluent. Yield 80%

EXAMPLE 43

Synthesis of 1,39-bis(1,3-dioxa-2-phenyl-5-cyclohexyloxy)-20,20-[19-(1,3-dioxa-2-phenyl-5-cyclohexyloxy)-2,5,8,11,14,17-hexaoxanonadecyl]-3,6,12,15,18,22,25,28,31,34,37-dodecanoxanonatriacontane

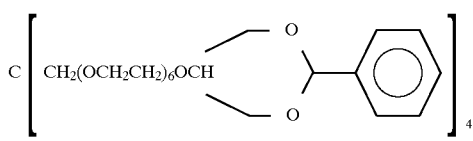
(Compound 43)

Compound 43 was obtained starting from 14,14-bis(2,5,8,11-tetraoxa-13-hydroxydecyl)-3,6,9,12,16,19,22,25-octaoxaheptacosan-1,27-diol, obtained as described in Example 3 of WO 95/25763, and compound 40, obtained as described in Example 39, following the procedure described in Example 40. Yield 75%.

EXAMPLE 44

Synthesis of 2,44-bis(hydroxymethyl)-23,23-bis[22-(hydroxymethyl)-2,5,8,11,14,17,20-heptaoxa-22-hydroxydocosyl]-3,6,9,12,15,18,21,25,28,31,34,37,40,43-tetradecaoxatritetracontan-1,45-diol.

$C[CH_2(OCH_2CH_2)_6OCH(CH_2OH)_2]_4$ (Compound 44)

Compound 44 was obtained by acid hydrolysis of compound 43, described in Example 43, following the procedure described in Example 41. The product was purified by column chromatography. Yield 95%

EXAMPLE 45

Synthesis of 1,57-(oxan-2-yl-oxy)-8,50-[7-(oxan-2-yl-oxy)-2,5-dioxaheptyl]-29,29-bis[28-(oxan-2-yl-oxy)-21-[7-(oxan-2-yl-oxy)-2,5-dioxaheptyl]-2,5,8,11,14,17,20,23,26-nonaoxadocosyl]-3,6,9,12,15,18,21,24,27,3 1,34,37,40,43, 46,49,52,55-decaotaoxaheptapentacontane.

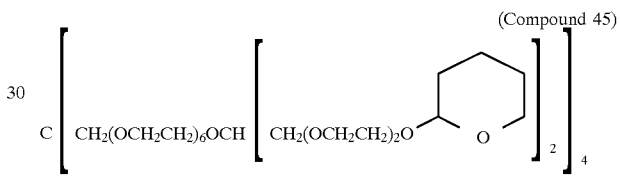
(Compound 45)

Compound 45 was obtained starting from compound 44, obtained as described in Example 44, and 2-(3-oxa-5-chloropentyloxy)oxane, prepared as described in Example 1 of WO 95/25763, following the synthetic procedure described in Example 6. The crude product was purified by column chromatography using a mixture of EtOAc/CH3OH as eluent. Yield 70%.

EXAMPLE 46

Synthesis of 8,50-[2,5-dioxa-7-hydroxyheptyl]-29,29-bis-[21-(2,5-dioxa-7-hydroxyheptyl)-2,5,8,11,14,17,20,23,26-nonaoxa-28-hydroxyoctacosyl]-3,6,9,18,21,24,27,31,34,37,40,43,46,49,52,55-decaotaoxaheptapentacontan-1,57-diol

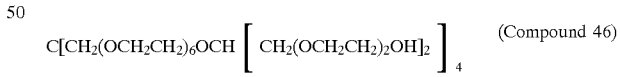
(Compound 46)

Compound 46 was obtained by acid hydrolysis of compound 45, described in Example 45, following the procedure described in Example 7. Yield 90%.

EXAMPLE 47

Synthesis of 1,69bis(1,3-dioxa-2-phenyl-5-cyclohexyloxy)-35,35-bis[34-(1,3-dioxa-2-phenyl-5-cyclohexyloxy)-21-[13-(1,3-dioxa-2-phenyl-5-cyclohexyloxy)-2,5,8,11-tetraoxatridecyl]-2,5,8,11,14,17,20,23,26,29,32-undecanoxatetratriacontyl]-14,56b-bis[13-(1,3-dioxa-2-phenyl-5-cyclohexyloxy)-2,5,8,11-tetraoxatridecyl]-3,6,9,12,15,18,21,24,27,30,33,37,40,43,46,49,52,55,58,61,64,67-docosaoxanonahexacontane

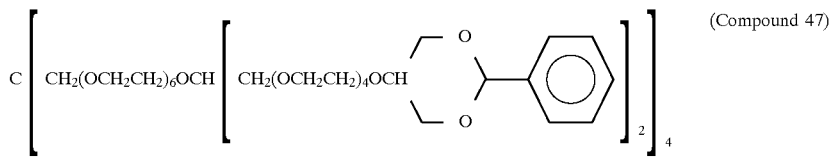
(Compound 47)

Compound 47 was obtained by reaction of compound 46, obtained as described in Example 46, and compound 40, obtained as described in Example 40, following the procedure described in Example 41. The crude product was purified by column chromatography using a mixture of acetone/EtOAc as eluent. Yield 80%.

EXAMPLE 48

Synthesis of 2,74-dihydroxymethyl-38,38-bis[36-hydroxymethyl-21[15-hydroxymethyl-2,5,8,11,14-pentaoxa-16-hydroxyhexadecyl]-2,5,8,11,14,17,20,23,26,29,32,35-dodecaoxa-37-hydroxyheptatriacontyl]-17,59-bis[15-hydroxymethyl-2,5,8,11,14-pentaoxa-16-hydroxyhexadecyl]-3,6,9,12,15,18,21,24,27,30,33,36,40,43,46,49,52,55,58,61,64,67,70,73-tetracosaoxapentaheptacontan-1,75-diol

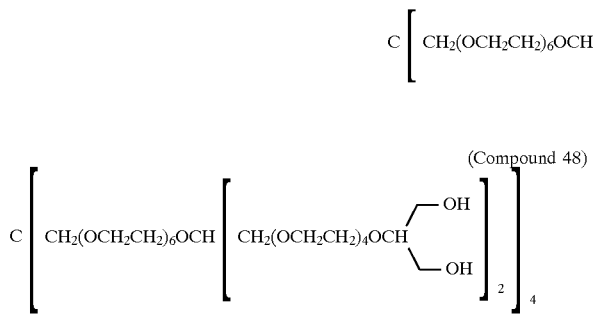
(Compound 48)

Compound 48 was obtained by acid hydrolysis of compound 47 following the procedure described in Example 42. The crude product was purified by column chromatography using a mixture of $CH_2Cl_2/CH_3OH/NH_3$ as eluent. Yield 70%.

EXAMPLE 49

Synthesis of 1,87-(oxan-2-yl-oxy)-8.80-bis[7-(oxan-2-yl-oxy)-2,5-dioxaheptyl]-23,65bis-[22-(oxan-2-yl-oxy)-15-[7-(oxan-2-yl-oxy)-2,5-dioxaheptyl]-2,5,8,11,14,17,20-heptaoxadocosyl]-44,44-bis[43-(oxan-2-yl-oxy)-36-[7-(oxan-2-yl-oxy)-2,5-dioxaheptyl]-23-[22-(oxan-2-yl-oxy)-15-[7-(oxan-2-yl-oxy)-2,5-dioxaheptyl]-2,5,8,11,14,17,20-heptaoxadocosyl]-2,5,8,11,14,17,20,23,26,29,32,35,38,41-tetradecaoxatritetracontyl]-3,6,9,12,15,18,21,24,27,30,33,36,39,42,46,49,52,55,58,61,64,67,70,73,76,79,82,85-octacosaoxaheptaoctacontane Compound 49 was obtained starting from compound 48, obtained as described in Example 48, and 2-(3-oxa-5-chloropentyloxy)oxane, prepared as described in Example 1 of WO 95/25763, following the procedure described in Example 6. The crude product was purified by column chromatography using a mixture of EtOAc/MeOH as eluent. Yield 65%.

EXAMPLE 50

Synthesis of 8,80-bis(2,5-dioxa-7-hydroxyheptyl)-44,44-bis[43-(2,5-dioxa-7-hydroxyheptl)-21-[15-(2,5-dioxa-7-hydroxyheptyl)-2,5,8,11,14,17,20-heptaoxa-22-hydroxydocosyl]-2,5,8,11,14,17,20,23,26,29,32,35,38,41-tetradecaoxa-43-hydroxytritetracontyl]-23,65bis-[15-(2,5-dioxa-7-hydroxyheptyl)-2,5,8,11,14,17,20-heptaoxa-22-hydroxydocosyl]-3,6,9,12,15,18,21, 24,27,30,33,36,39,42,46,49,52,55,58,61,64,67,70,73,76,79,82,85-octacosaoxaheptaoctacontan-1,87-diol

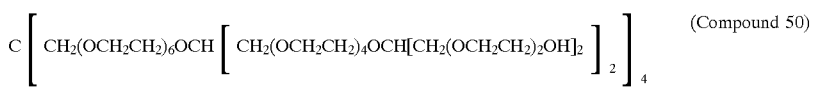
(Compound 50)

Compound 50 was obtained by acid hydrolysis of compound 49, described in Example 49, following the procedure described in Example 7. Yield 90%.

EXAMPLE 51

Compound 19 and 21, described in Example 19 and 21, were also obtained by a different synthetic pathway, following the procedure described in Example 41.

| Compound | Purification | Yield |
|---|---|---|
| 19 | Silica gel column, eluent EtOAc/acetone 7/3 | 60% |
| 21 | Silica gel column, eluent: EtOAc/MeOH 8/2 | 50% |

The corresponding hydroxy derivatives, compounds 20 and 22, were obtained, in comparable yields, following the procedure described in Example 42.

EXAMPLE 52

Synthesis of 1,51-bis(1,3-dioxa-2-phenyl-5-cyclohexyloxy)-26,26-bis[25-(1,3-dioxa-2-phenyl-5-cyclohexyloxy)-18-[7-(1,3-dioxa-2-phenyl-5-cyclohexyloxy)-2,5-dioxaheptyl]-9-[16-(1,3-dioxa-2-phenyl-5-cyclohexyloxy)-9-[7-(1,3-dioxa-2-phenyl-5-

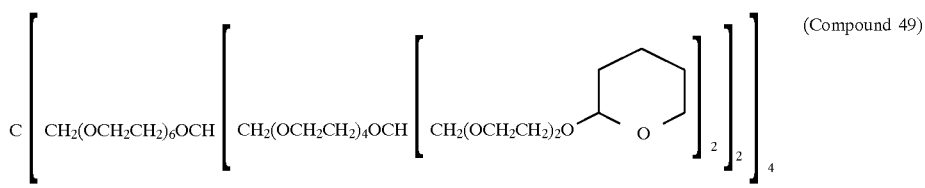
(Compound 49)

cyclohexyloxy)-2,5-dioxaheptyl]-2,5,8,11,14-pentaoxahexadecyl]-2,5,8,11,14,17,20,23- octaoxapentacosyl]-8,44-[7-(1,3-dioxa-2-phenyl-5-cyclohexyloxy)-2,5-dioxaheptyl]-17,35-[16-(1,3-dioxa-2-phenyl-5-cyclohexyloxy)-9-[7-(1,3-dioxa-2-phenyl-5-cyclohexyloxy)-2,5-dioxaheptyl]-2,5,8,11,14-pentaoxahexadecyl]-3,6,9,12,15,18,21,24,28,31,34,37,40,43,46,49-hexadecaoxahenpentacontane.

octaoxahexacosyl]-18-[16-(2-phenyl-1,3-dioxacyclohexyl)-9-(7-(2-phenyl-1,3-dioxacyclohexyl)2,5-dioxaheptyl)-2,5,8,11,14-pentaoxahexadecyl]-2,5,8,11,14,17,20,23,26,29,32-undecanoxatetratriacontyl]-3,6,9,12,15,18,21,24,27,30,33,37,40,43,46,49,52,55,58,61,64,67-docosaoxanonahexacontane

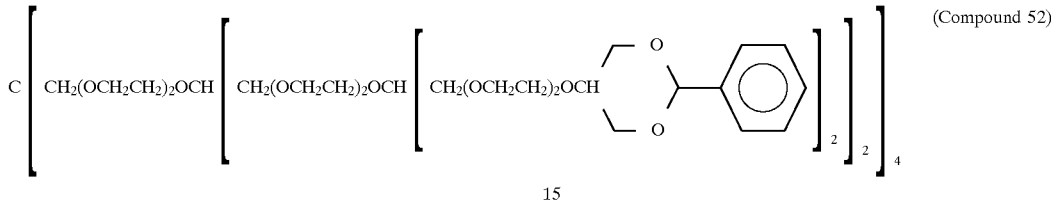
(Compound 52)

Compound 52 was obtained by reaction of compound 21, described in Example 51, and compound 40 described in Example 40, following the procedure described in Example 41. Yield 50%.

EXAMPLE 53

Synthesis of 2,56-dihydroxymethyl-29,29-bis[37-ydroxymethyl-9[18-hydroxymethyl-9-[9-hydroxymethyl-2,

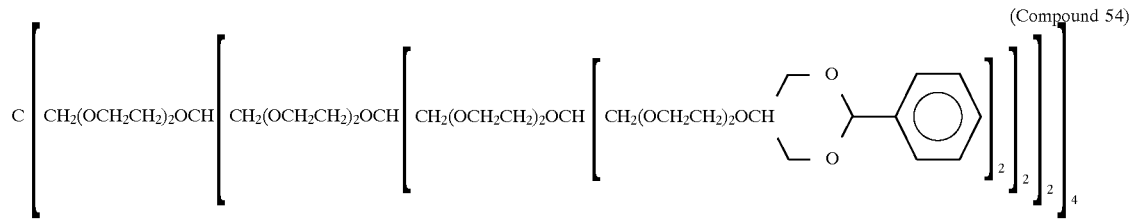
(Compound 54)

5,8-trioxa-10-hydroxydecyl]-2,5,8,11,14,17-hexaoxa-19-hydroxynonadecyl]-18-[9-hydroxymethyl-2,5,8-trioxa-10-hydroxydecyl]2,5,8,11,14,17,20,23-26-nonaoxa-28-hydroxyoctacosyl]-20,38-bis[18-hydroxymethyl-9-[9-hydroxymethyl-2,5,8-trioxa-10-hydroxydecyl]-2,5,8,11,14,17-hexaoxa-19-hydroxynonadecyl]-11,47-bis[9-hydroxymethyl-2,5,8-trioxa-10-hydroxydecyl]-3,6,6,12,15,18,21,24,27,31,34,37,40,43,46,49,52,55-octadecaoxaheptapentacontan-1,57-diol

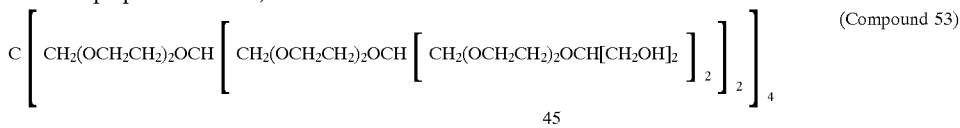
(Compound 53)

Compound 53 was obtained by acid hydrolysis of compound 52 following the procedure described in Example 42. Yield 85%.

EXAMPLE 54

Synthesis of 1,69-bis(2-phenyl-1,3-dioxacyclohexyl)-8,62-bis[7-(2-phenyl-1,3-dioxacylohexyl)-2,5-dioxaheptyl]-26,44-bis[25-(2-phenyl-1,3-dioxacyclohexyl)-18-(7-(2-phenyl-1,3-dioxacyclohexyl)-2,5-dioxaheptyl)-9-(16-(2-phenyl-1,3-dioxacyclohexyl)-2,5,8,11,14-pentaoxahexadecyl)- 2,5,8,11,14,17,20,23-octaoxahexacosyl]-17,53-bis[16-(2-phenyl-1,3-dioxacyclohexyl)-9-(7-(2-phenyl-1,3-dioxacyclohexyl)2,5-dioxaheptyl)-2,5,8,11,14-pentaoxahexadecyl]-35,35-bis[34-(2-phenyl-1,3-dioxacyclohexyl)-27-[7-(2-phenyl-1,3-dioxacyclohexyl)-2,5-dioxaheptyl]-9-[25-(2-phenyl-1,3-dioxacyclohexyl)-18-(7-(2-phenyl-1,3-dioxacyclohexyl)-2,5-dioxaheptyl)-9-(16-(2-phenyl-1,3-dioxacyclohexyl)-2,5,8,11,14-pentaoxahexadecyl)-2,5,8,11,14,17,20,23-

Compound 54 was obtained starting from compound 53 and compound 40 following the procedure described in Example 41. Yield 50%.

EXAMPLE 55

Synthesis of 2,74-dihydroxymethyl-38,38-bis[36-hydroxymethyl-9[27-hydroxymethyl-9-(18-hydroxymethy-9-(9-hydroxymethyl-2,5,8-trioxa-10-hydroxydecyl)-2,5,8,11,14,17-hexaoxa-19-hydroxynonadecyl)-18-(9-hydroxymethyl-2,5,8-trioxa-10-hydroxydecyl)-2,5,8,11,14,17,20,23,26-nonaoxa-28-hydroxyoctacosyl]-18-[18-hydroxymethyl-9-(9-hydroxymethyl-2,5,8-trioxa-10-hydroxydecyl)-2,5,8,11,14,17-hexaoxa-19-hydroxynonadecyl]-27-(9-hydroxymethyl-2,5,8-trioxa-10-hydroxydecyl)-2,5,8,11,14,17,20,23,26,29,32,35-dodecaoxa-37-hydroxyheptatriacontyl]-29,57-bis[27-hydroxymethyl-9-(18-hydroxymethyl-9-(9-hydroxymethyl-2,5,8-trioxa-10-hydroxydecyl)-2,5,8,11,14,17-hexaoxa-19-hydroxynonadecyl)-18-(9-hydroxymethyl-2,5,8-trioxa-10-hydroxydecyl)-2,5,8,11,14,17,20,23,26-nonaoxa-28-hydroxyoctacosyl]-20,56-bis[18-hydroxy-methyl-9-(9-hydroxymethyl-2,5,8-trioxa-10-hydroxy-decyl)-2,5,8,11,14, 17-hexaoxa-19-hydroxynonadecyl]-11,65-bis[9-hydroxymethyl-2,5,8-trioxa-10-hydroxydecyl]-3,6,9,12,15,18,21,24,27 30,33,36,40,43,46,49,52,55,58,61,64,67,70,73-tetracosaoxapentaheptacontan-1,75-diol.

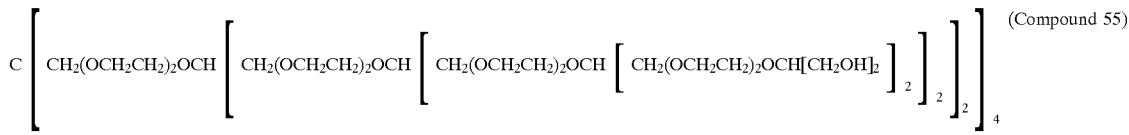

(Compound 55)

Compound 55 was obtained by hydrolysis of compound 54 following the procedure described in Example 42. Yield 70%

Using the described procedures, as such or after slight modification evident to the expert technician, the following products were obtained:

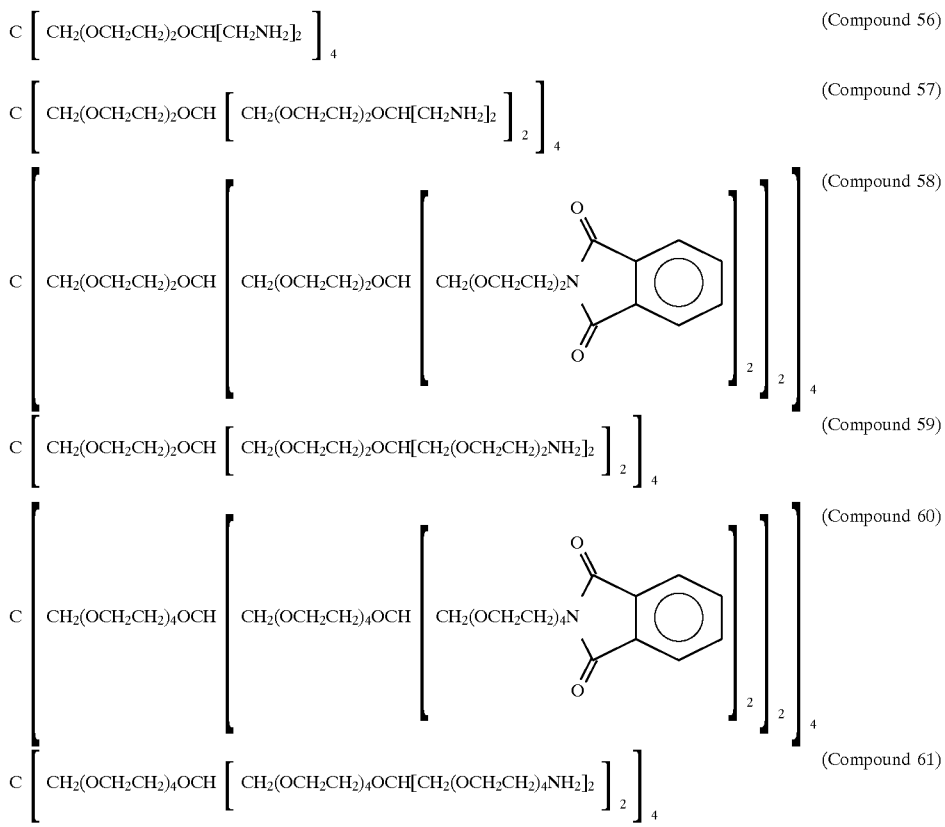

References

1) Tomalia, D. A., Naylor, A. M., and Goddard III, W. A. (1990) *Angew. Chem. Int. Ed. Engl.* 29, 138–175.
2) Tomalia, D. A., Baker, H., Dewald, J., Hall, M., Kallos, G., Martin, S., Roeck, J., Ryder, J., and Smith, P. (1985) *Polymer Journal* 17, 117–132.
3) Smith, P. B., Martin, S. J., Hall, M. J., and Tomalia, D. A. In J. Mitchell, Jr., (Ed.): Applied Polymer Analysis and Characterization, Hanser, München/New York 1987, 357–385.
4) Tomalia, D. A., Dewald, J. R. (1986) U.S. Pat. No. 4,587,329.
5) Padias, A. B., Hall Jr., H. K., Tomalia, D. A., and McConnel, J. R. (1987) *J. Org. Chem.* 52, 5305–5312.
6) Denkewalter, R. G., Kolc, J., Lukasavage, W. J. (1981) U.S. Pat. No. 4,289,872.
7) Newkome, G. R., Yao, Z., Baker, G. R., and Gupta, V. K. (1985) *J. Org. Chem.* 50, 2003–2004.
8) Newkome, C. R., Yao, Z., Baker, G. R., Gupta, V. K., Russo. P. S. and Saunders, M. J. (1986) *J. Amer. Chem. Soc.* 108, 849–850.
9) Newkome, G. R., Baker, G. R., Arai, S., Saunders, M. J., Russo, P. S., Therid, K. J. (1990) *J. Amer. Chem. Soc.* 112, 8458–8465.
10) Newkome, G. R., Moorefield, C. N., Baker, G. R., Johnson, A. L., and Behera, R. K. (1991) *Angew. Chem. Int. Ed. Engl.* 30, 1176–1178.
11) Newkome, G. R., Moorefield, C. N., Baker, G. R., Saunders, M. J., and Grossman, S. H. (1991) *Angew. Chem. Int. Ed. Engl.* 30, 1178–1180.
12) Newkome, G. R., Lin, X., and Young, J. K. (1992) *Synlett*, 53–54.
13) Hawker, C. J., and Frechet, J. M. J. (1990) *J. Am. Chem. Soc.* 112, 7628–7647.
14) Frechet, J. M. J., Hawker, C. J., Philippide, A. E. (1991) U.S. Pat. No. 5,041,516.
15) Wooley, K. L., Hawker, C. J., and Frechet, J. M. J. (1991) *J. Am. Chem. Soc.* 113, 4252–4261.
16) Wooley, K. L., Hawker, C. J., and Frechet, J. M. J. (1991) *J. Chem. Soc. Perkin. Trans. I*, 1059–1076.

17) Frechet, J. M. J., Hawker, C. J., Uhrich, K. (1992) Patent Appl. WO 9208749.
18) Hawker, C. J., and Frechet, J. M. J. (1992) *J. Chem. Soc. Perkin. Trans. I*, 2459–2469.
19) Frechet, J. M. J., Hawker, C. J., Wooly, K. (1993) Patent Appl. WO 9321259.
20) Buhleier, E., Wehner, W., and Vogtle, F. (1978) *Synthesis* 155–158.
21) Miller, T. M., Neenan, T. X., Zayas, R., and Bair, H. E. (1992) *J. Am. Chem. Soc.* 114, 1018–1025.
22) Uchida, H., Kabe, Y., Yoshino, K., Kawamata, A., Tsumuraya, T., and Masamune, S. (1990) *J. Am. Chem. Soc.* 112, 7077–7079.
23) Mathias, L. J., and Carothers, T. W. (1991) *J. Am. Chem. Soc.* 113, 4043–4044.
24) Rengan, K., and Engel, R. (1991) *J. Chem. Soc. Perkin Trans. I*, 987–990.
25) Rengan, K., and Engel, R. (1992) *J. Chem. Soc. Chem. Commun.*, 757–758.
26) Morikawa, A., Kakimoto, M., and Imai, Y. (1991) *Macromolecules* 24, 3469–3474.
27) Nagasaki, T., Ukon, M., Arimori, S., and Shinkai, S. (1992) *J. Chem. Soc. Chem. Commun.* 608–610.
28) Serroni, S., Denti, G., Campagna, S., Juris, M., Ciano, M., and Balzani, V., (1992) *Angew. Chem. Int. Ed. Engl.* 31, 1493–1495.
29) Newkome, G. R., Moorefield, C. N., Behera, R. K. (1993) Patent Appl. WO 9321144.
30) De Brabander-van den Berg, E. M. Mejier, E. W., Vandenbooren, F. H., Bosman, H. J. (1993) Patent Appl. WO 9314147.

We claim:

1. Dendrimeric macromolecules of formula (I)

$$A[G_{(1 \to p)}]_r \quad (I),$$

having r number of structures $G_{(1 \to p)}$ in the dendrimer structure, where:

A is a polyfunctional/polyvalent central nucleus, or core, which is an aliphatic open chain, branched or unbranched, or an alicyclic, or a heterocyclic group containing N, O and/or S, or an aromatic or a heteroaromatic group and which contains terminal groups to which polyoxaethylene chains of a first generation shell are attached, r is an integer from 3 to 5 representing the multiplicity of the core, $G_{(1 \to p)}$ is a single dendron linked to A, $[G_{(1 \to p)}]_r$ represents the branched structure of the macromolecule comprising p levels of generation shells, from the first one $g_{(1)}$ to the last one $g_{(p)}$, in which the total number p of said generation shells can range from 1 to 20 and in which the different generation shells may contain the same repetition units, and in which:

(a) each generation $g_{(i)}$, except for the last $g_{(p)}$, comprises repeating units, which are represented by functional groups of formula

—B—M— where:
B is a polyoxaethylene chain of formula:

in which n can range from 0 to 25 and may differ from generation shell to generation shell and in which, in at least one generation shell of the macromolecule, n is other than 0, M represents a binary branching point, which is a polyvalent aliphatic group comprising 2 reactive functional groups for the linking of the polyoxaethylene chains of the next generation shell, (b) the last generation shell, $g_{(p)}$, comprises functional groups of formula:

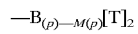

where $B_{(p)}$ and $M_{(p)}$, are defined analogously to B and M and where the 2 reactive groups of $M_{(p)}$ are connected to groups T in which T is a terminal group that is either H or halo, hydroxyl, amino, thiol, —O-tosyl, —O-mesyl, —O-tresyl, —O-brosyl, trifluoromethansulfonyl, aldehydo, carboxy, or an amido group, said terminal group T being free, either dissociated or undissociated, or protected by a protective group, or $M_{(p)}$ is a single bond, no branching exists and the last generation shell $g_{(p)}$, is formed by groups of formula:

—$B_{(p)}$—T where $B_{(p)}$ and T are as above defined, and (c) when p=1, the macromolecule contains only one generation shell, $g_{(p)}$, which corresponds to $g_{(1)}$ and has the formula:

where $B_{(1)}$ and $M_{(1)}$ are defined analogously to $B_{(p)}$ and $M_{(p)}$ and T is as above defined, as well as the corresponding derivatives labelled with isotopes such as $^{13}C$, $^{14}C$, $^2H$, $^3H$ and 125I.

2. Macromolecules according to claim 1, in which:

a) A is a neopentyl group of formula

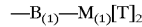

b) B is a group of formula

in which n is an integer from 0 to 20, provided that in at least one generation shell n is other than 0 and c) M is a group of formula

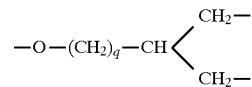

in which q=0.

3. Macromolecules according to claim 1, of formula (III)

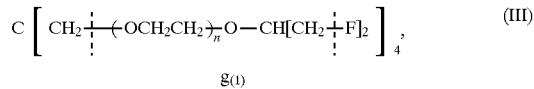 (III)

in which:

n is an integer from 0 to 15, provided that in at least one generation shell n is other than 0, $g_{(1)}$ is the first generation shell, F is T, or the sequence of successive generation shells from $g_{(2)}$ to $g_{(p)}$, in which the last generation shell, $g_{(p)}$, comprises groups of formula —$(OCH_2CH_2)_n$—OCH[$CH_2$—T]$_2$ or groups of formula —$(OCH_2CH_2)_n$—T and T is as above defined, and the total number of generation shells p can be as high as 15.

4. Compounds according to claim 3, selected from the group consisting of compounds from 2 to 38 and from 41 to 61 of the ones described in the experimental examples.

* * * * *

UNITED STATES PATENT AND TRADEMARK OFFICE
CERTIFICATE OF CORRECTION

PATENT NO. : 5,886,110
DATED : March 23, 1999
INVENTOR(S) : Gozzini et al

It is certified that error appears in the above-identified patent and that said Letters Patent is hereby corrected as shown below:

Title page Item [62] delete "Division" insert --Continuation-in-part--.

Signed and Sealed this

Thirteenth Day of July, 1999

Attest:

Q. TODD DICKINSON

Attesting Officer

Acting Commissioner of Patents and Trademarks